(12) United States Patent
Chan et al.

(10) Patent No.: US 7,647,122 B2
(45) Date of Patent: Jan. 12, 2010

(54) SURGICAL NEEDLE DRIVER

(75) Inventors: Cygni Chan, Shoreview, MN (US); Carl A. Schu, Plymouth, MN (US); Orhan Soykan, Shoreview, MN (US); Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 806 days.

(21) Appl. No.: 11/189,490

(22) Filed: Jul. 26, 2005

(65) Prior Publication Data
US 2007/0023305 A1    Feb. 1, 2007

(51) Int. Cl.
*A61N 1/00* (2006.01)
(52) U.S. Cl. .................. 607/116; 206/366; 606/222
(58) Field of Classification Search .............. 607/116, 607/115, 185, 186, 187, 188, 189, 222; 128/907
See application file for complete search history.

(56) References Cited

U.S. PATENT DOCUMENTS

| | | | |
|---|---|---|---|
| 3,037,619 A * | 6/1962 | Stevans | 206/63.3 |
| 4,341,226 A * | 7/1982 | Peters | 607/132 |
| 4,922,924 A | 5/1990 | Gambale et al. | |
| 5,086,787 A | 2/1992 | Grandjean et al. | |
| 5,241,957 A | 9/1993 | Camps et al. | |
| 5,257,999 A | 11/1993 | Slanetz, Jr. | |
| 5,300,110 A | 4/1994 | Latterell et al. | |
| 5,304,185 A | 4/1994 | Taylor | |
| 5,324,323 A | 6/1994 | Bui | |
| 5,423,876 A | 6/1995 | Camps et al. | |
| 5,489,294 A | 2/1996 | McVenes et al. | |
| 5,601,575 A | 2/1997 | Measamer et al. | |
| 5,683,429 A | 11/1997 | Mehra | |
| 5,702,359 A * | 12/1997 | Hofmann et al. | 604/20 |
| 5,824,028 A | 10/1998 | Knisley | |
| 5,928,278 A | 7/1999 | Kitschmann | |
| 5,984,932 A | 11/1999 | Yoon | |
| 5,993,466 A | 11/1999 | Yoon | |
| 6,071,289 A | 6/2000 | Stefanchik et al. | |
| 6,159,224 A | 12/2000 | Yoon | |
| 6,418,341 B1 * | 7/2002 | Hofmann et al. | 604/21 |
| 6,434,431 B1 | 8/2002 | Camps et al. | |
| 6,656,205 B1 | 12/2003 | Manhes | |
| 6,689,047 B2 | 2/2004 | Gellman | |
| 2003/0004523 A1 * | 1/2003 | Chan et al. | 606/148 |
| 2003/0195600 A1 | 10/2003 | Tronnes et al. | |
| 2005/0043766 A1 | 2/2005 | Soykan et al. | |
| 2006/0052857 A1 | 3/2006 | Osypka | |
| 2007/0027512 A1 | 2/2007 | Chan et al. | |
| 2007/0027513 A1 | 2/2007 | Chan et al. | |

OTHER PUBLICATIONS

Office Action dated Jun. 14, 2007 for U.S. Appl. No. 11/189,447 (9 pgs.).
Responsive Amendment dated Sep. 14, 2007 for U.S. Appl. No. 11/189,447 (14 pgs.).

* cited by examiner

*Primary Examiner*—Carl H. Layno
*Assistant Examiner*—Jon-Eric C. Morales
(74) *Attorney, Agent, or Firm*—Shumaker & Sieffert, P.A.

(57) ABSTRACT

A needle driver is described that can be used to drive a plurality of surgical needles into or proximate to tissue of a living body. The needle driver assists the surgeon in perforating the tissue, creating the tracts at a desired depth, and creating multiple tracts simultaneously. The needle driver is configured to hold the needles securely when creating the tracts, and is also configured to disengage from the needles after the tracts have been created.

18 Claims, 15 Drawing Sheets

SURGICAL NEEDLE DRIVER

TECHNICAL FIELD

The present invention relates to medical devices, and in particular, to devices associated with surgical needles.

BACKGROUND

There are a number of situations in which it is desirable to electrically stimulate tissue of a living body. Target tissues for stimulation can include skeletal muscle, smooth muscle, nerves and organs. In addition, organs such as the stomach and heart can respond to therapy that includes electrical stimulation. It is often desirable to implant stimulating electrodes in or proximate to the target tissue. It is also often desirable to stimulate the target tissue without stimulating neighboring tissues.

An application in which it is desirable to stimulate a region of target tissue while avoiding stimulation of surrounding tissue is stimulation of the myocardium. For example, following a heart attack, cardiac tissue can become necrotic and cease contributing to hemodynamic function. Numerous morbid conditions are sequelae of the loss of hemodynamic function. The necrosis can be treated with cell therapy, which involves transplanting cells into the damaged myocardium to repopulate the damaged region. In one procedure, cells are transplanted by injection directly into or proximate to the affected tissue. Electrical stimulation of the region having the transplanted cells can cause the transplanted cells to contract and assist in hemodynamic function. Electrical stimulation might also increase the cell viability, cell engraftment and cell proliferation. The cells transplanted include but are not limited to skeletal myoblast cells, cardiac myoblast cells and stem cells.

In such a case, it is desirable to electrically stimulate the region with the transplanted cells, but not the heart as a whole. Stimulation of the heart as a whole can cause unwanted or poorly timed contractions of the heart, and possibly life-threatening conditions such as ventricular fibrillation.

Similar concerns can apply in other applications as well. It may be desirable to implant electrodes in the wall of the stomach, for example, to induce contraction or other physiological effect, without stimulating neighboring muscles, organs or nerves.

SUMMARY

In general, the invention is directed to a needle driver that can be used to drive a plurality of surgical needles into or proximate to the target tissue. One exemplary use for such a needle driver is to create a plurality of parallel, regularly spaced tracts in the tissue to receive stimulation electrodes. The needle driver assists the surgeon in perforating the tissue, creating the tracts at a desired depth, and creating multiple tracts simultaneously. The needle driver is configured to hold the needles securely when creating the tracts, and is also configured to disengage from the needles after the tracts have been created.

The needle driver can include plurality of trenches, each trench configured to receive a surgical needle. A desired number of needles can be loaded into the needle driver. The needle driver includes a cover than can be closed to secure the needles in the trenches. The cover can also be opened so that needles can be loaded into or disengaged from the needle driver.

The invention supports embodiments in which the needle driver comes pre-loaded in a hermetically sealed package. The needle driver can be pre-packaged and pre-sterilized, and the surgeon can select the package that is best suited to the patient's needs. During a surgical procedure, the package can be opened, a needle cap or caps that protect the tips of the needles can be removed, and the needle driver is ready for use.

In a typical surgical procedure, a surgeon grips the needle by a grippable structure and perforates the tissue with several needles at one time. In some embodiments of the invention, the needle driver includes a stabilizer that helps stabilize the tissue and control the depth of the tracts in the tissue. After the tracts are created, the surgeon disengages the needle driver from the needles and removes the needle driver from the surgical field.

The invention also supports embodiments in which the needle driver is configured to drive needles at different depths. By including trenches of differing depths, for example, a needle driver can drive several needles in a non-planar fashion.

In one embodiment, the invention presents a device comprising a main body having a plurality of trenches, each of the trenches configured to receive a respective one of a plurality of surgical needles. The device also includes a cover configured to assume an open position and a closed position, wherein the cover in the open position is configured to permit insertion of the surgical needles in the trenches and removal of the surgical needles from the trenches. The cover in the closed position is configured to secure the surgical needles in the trenches.

In another embodiment, the invention is directed to a device comprising a loaded needle driver and a package that contains the loaded needle driver. The loaded needle driver comprises a main body having a plurality of trenches, each of the trenches configured to receive a surgical needle, a cover configured to assume an open position and a closed position, and at least one surgical needle comprising a proximal end and a distal tip, the proximal end of the surgical needle secured in at least one trench.

The invention may result in one or more advantages. A surgeon can use the invention to create several spaced tracts in tissue in an efficient manner. The needle driver can be readily disengaged from the needles after the tracts are created. A stabilizer can help stabilize the tissue and control the depth of the tracts in the tissue. In some embodiments, the stabilizer can be moved or otherwise adjusted, or removed completely should it become a hindrance Although the invention is described in connection with electrode implantation, the invention is not limited to that particular use. The details of one or more embodiments of the invention are set forth in the accompanying drawings and the description below. Other features, objects, and advantages of the invention will be apparent from the description and drawings, and from the claims.

DETAILED DESCRIPTION

Various organs or tissues in a human or animal body can benefit from electrical stimulation. In various applications, electrical stimulation can induce contraction in cardiac muscle, smooth muscle and skeletal muscle. Electrical stimulation can be used to apply neurostimulation, or to trigger various reflexes, or to cause an organ to perform a function. The invention is not limited to any particular organ, tissue or location in the body.

Figure 1:
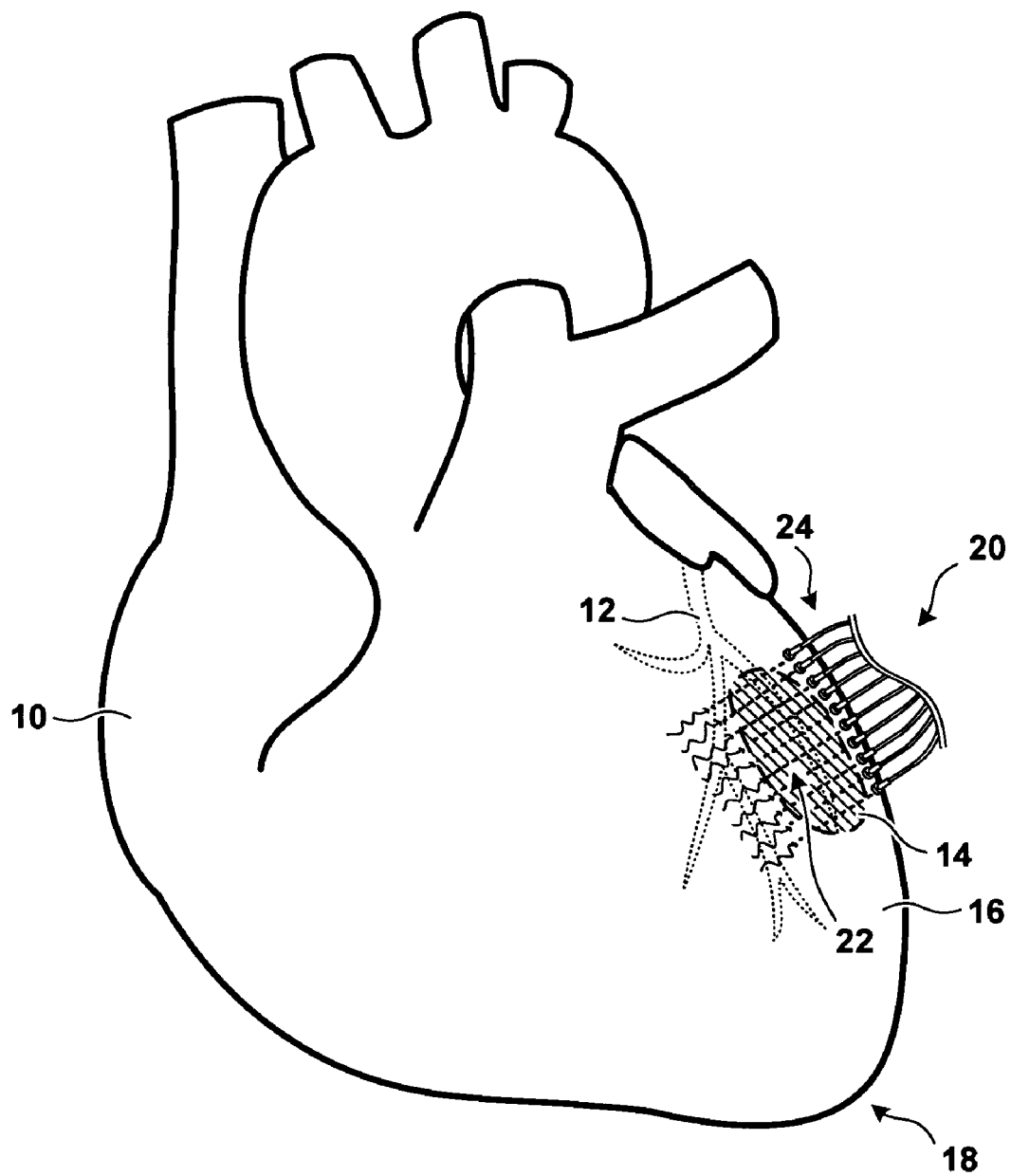
FIG. 1 is an illustration of a human heart showing deployment of leads and electrodes according to an embodiment of the invention.

FIG. 1 is a schematic diagram of a human heart 10. Although FIG. 1 depicts the invention in the context of heart 10, the invention is not limited to application with heart 10, and may be applied with any other organ or tissue in a human or animal body. FIG. 1 does show, however, a manner in which the invention can be used to apply electrical stimulation to a localized area or a target tissue.

A blockage in a branch of coronary artery 12 has deprived some tissue of heart 10 of a blood supply, and consequently of oxygen. As a result, the myocardial tissue deprived of oxygen has become damaged. In particular, some tissue has become necrotic, and an infarct region 14 has developed. In the example shown in FIG. 1, infarct region 14 is on the epicardium of the left ventricle 16.

Necrotic tissue does not contribute to the pumping action of heart 10. In particular, infarcted tissue does not contract in response to the excitation that takes place during a cardiac cycle. Normally, a ventricular excitation propagates from proximate to the apex 18 throughout the ventricular myocardium via gap junctions in the cardiac muscle, and the cardiac muscle contracts. The excitation does not cause infarct region 14 to contract, however. On the contrary, infarct region 14 can disrupt the propagation of the excitation, thereby affecting the excitation of healthy cardiac muscle. Moreover, scar tissue in infarct region 14 is usually less elastic than cardiac muscle, and can impair the function of heart 10 during the systolic and diastolic phases.

In the example of FIG. 1, infarct region 14 has been repopulated with transplanted biological material. The biological material, which may be transplanted into, transplanted proximate to or transplanted around the necrotic tissue, may include any of several biological substances, singly or in combination. The biological material may include cells, such as skeletal myoblasts, precursor cells, endothelial cells, differentiated or undifferentiated stem cells, undifferentiated contractile cells, fibroblasts and genetically engineered cells. The biological material may further comprise components of cells, such as genetic material, genetic vectors such as viruses, or proteins such as Insulin-Like Growth Factor or other growth factors. The biological material may also include a chemoattractant to attract precursor cells from the heart or from the other organs to infarct region 14. These categories of biological material are not exclusive of one another, and a particular element of biological material may belong to more than one category. Also, the transplanted biological material need not be exclusively biological, but may include an inorganic or engineered material, such as a scaffold to hold biological material. Furthermore, the invention is not limited to the particular materials listed herein.

Nor is the invention limited to any particular transplantation technique. For a typical patient, a surgeon may transplant biological material by injection during a surgical procedure, such as an open-heart procedure. The surgeon may inject the biological material into the necrotic tissue or proximate to the necrotic tissue. The surgeon may also deliver the biological material through the coronary vasculature. In practice, implanted cells have been observed to migrate, so over time some biological material transplanted in infarct region 14 may migrate outside infarct region 14. In addition, biological material transplanted in infarct region 14 may migrate to a different site inside infarct region 14.

An electrode system 20 is deployed proximate to infarct region 14. Electrode system 20, which will be described in more detail below, comprises one or more electrodes 22 deployed intramyocardially, i.e., embedded in the tissue of the heart 10. Electrodes 22 are coupled to an implantable medical device (IMD) such as an implantable pulse generator (IPG) (not shown) that delivers electrical stimulation to the transplanted biological material. In particular, electrodes 20 are deployed so that an electrical stimulation delivered to the myocardium via electrodes 20 creates a difference in electrical potential, which in turn generates an electrical field that captures contractile fibers of the transplanted biological material. As a result, electrodes 20 cause the contractile fibers to induce a contraction in a direction that aids hemodynamic function.

Transplanted contractile biological material tends to orient itself in the direction in which the tissue stretches. Accordingly, the contractile fibers of the transplanted material generally will, with time, align with nearby cardiac muscle fibers. It is not necessary that all transplanted biological material contributes to contraction. Undifferentiated cells, for example, may undergo differentiation in response to stimulation, and may develop contractile capability or increase in number. Also, some transplanted biological material may support the contractile biological material. Endothelial cells, for example, may promote vascularization in or around infarct region 14, and genetic material may promote differentiation or phenotypic conversion of other cells.

In general, it can be desirable to deliver stimulations at a time when the transplanted biological material can contribute to hemodynamic function, such as when heart 10 is in the ejection phase of the cardiac cycle. If the transplanted material is stimulated at the time of ventricular activation, it is possible that the transplanted material will contract and relax prior to any pumping of blood. By waiting for the ejection phase to begin, stimulation can cause the transplanted material to contract at a time when the contraction of the transplanted material can contribute to pumping of blood. Various techniques may be employed to determine whether heart 10 is in the ejection phase, such as monitoring the electrical signals of heart 10 and monitoring ventricular blood pressure.

Further, it can be desirable that the stimulations delivered to the transplanted biological material comprise one or more stimulating pulses. Such stimulating pulses may be distinct from the stimulations that would be applied to cardiac tissue by a pacemaker. In particular, stimulations of the transplanted biological material may comprise several stimulation pulses in rapid succession to produce a sustained tetanic contraction.

It is also desirable that the stimulations delivered to the transplanted material via electrode system 20 be substantially focused on the repopulated zone where the biological material has been transplanted. In other words, it is generally undesirable for electrode system 20 to stimulate healthy cardiac tissue or nearby tissue such as the chest muscles. Stimulation of healthy cardiac tissue can cause the tissue to begin a contraction, and in some cases can create currents that induce fibrillation.

The electrical field generated by electrode system 20 is such that the electrical field can be customized to the particular region of tissue for which stimulation is desired. As a result, stimulations can be targeted to the region where transplanted biological material is present, with less risk of stimulation of healthy cardiac tissue.

Although FIG. 1 shows electrode system 20 deployed in the tissue of heart 10, the invention is not limited to cardiac application. The invention can be used to stimulate other organs, as well as muscles and nerves. For example, electrode system 20 may be deployed in the tissue of a stomach and can be used to stimulate various stomach activities. As with heart 10, the stimulations can be targeted to a desired region of tissue.

Furthermore, although FIG. 1 shows electrode system 20 employing a plurality of electrodes, the invention is not limited to any number of electrodes.

Figure 2:
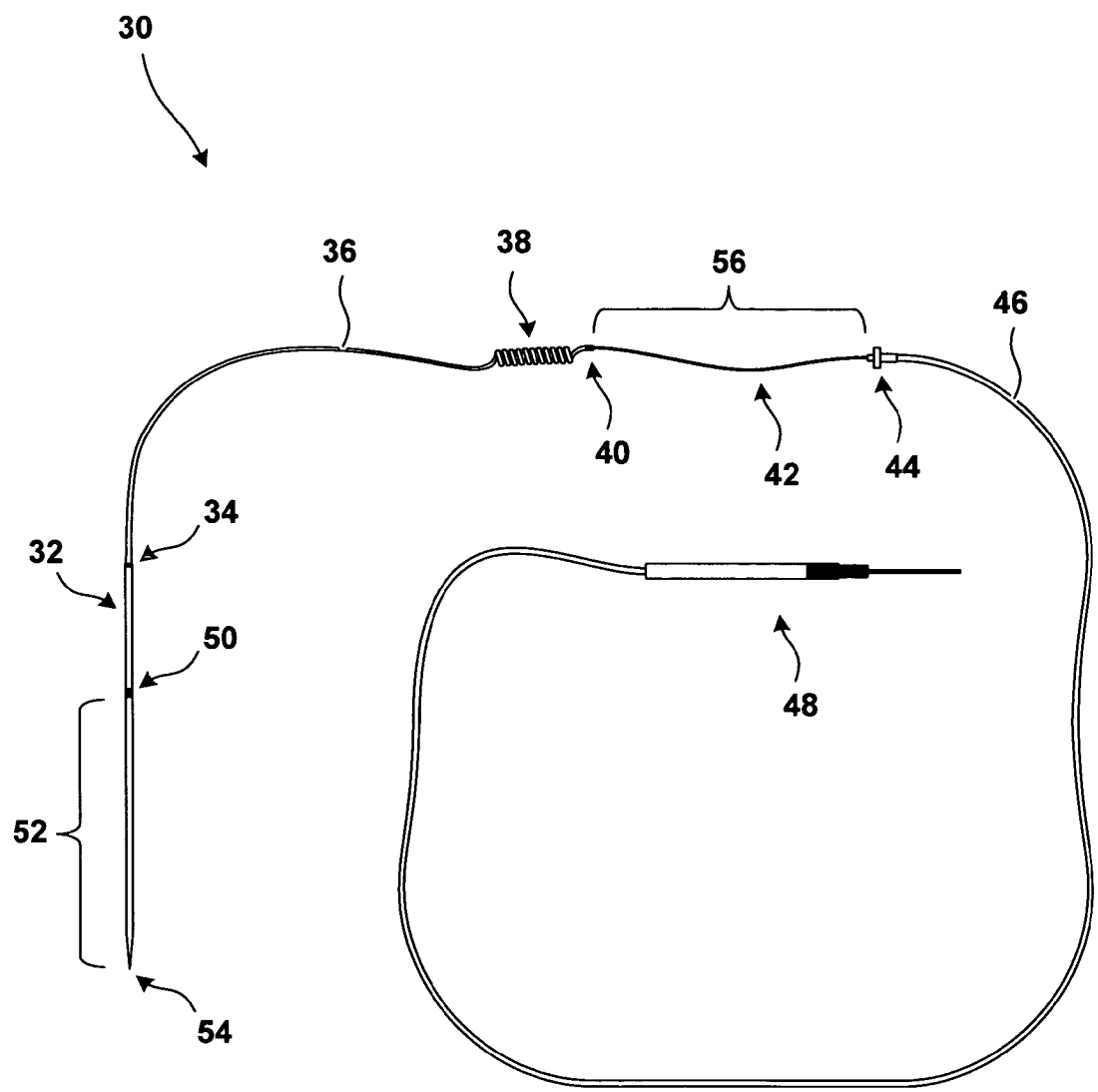
FIG. 2 is a schematic illustration of an electrode assembly.

FIG. 2 is a schematic diagram illustrating a single electrode assembly 30. Electrode system 20 in FIG. 1 can be deployed using a plurality of electrode assemblies 30. For purposes of description, the distal end of electrode assembly 30 is farthest away from an IMD to which electrode assembly 30 may be coupled, and the proximal end of electrode assembly 30 is closest to the IMD. In the description that follows, components of electrode assembly 30 will be identified, then individual components will be discussed in detail.

At the distal end, electrode assembly 30 comprises a surgical introduction needle 32. At its proximal end, introduction needle 32 is physically coupled by a connecting element 34 to a flexible threadlike leader 36. Leader 36 is coupled to a fixation mechanism, depicted in FIG. 2 as a set of helical coils or "pigtail" 38. In the embodiment shown in FIG. 2, pigtail 38 is formed from the proximal end of leader 36, and is not coupled to leader 36 with a coupling element. The invention encompasses embodiments in which leader 36 and pigtail 38 are coupled by a distinct coupling element, however. Pigtail 38 is coupled by a second coupling element 40 to an elongated electrode 42. As shown in FIG. 2, electrode 42 is uninsulated.

Coupled to electrode 42 is a stopper 44, which is proximate to an insulated lead body 46. Insulated lead body 46 can be physically coupled to the proximal end of electrode 42, the proximal end of stopper 44, or both. At the proximal end of lead body 46 is an IPG connector 48, such as an IS-1 standard connector, configured to electrically couple electrode assembly 30 to an IMD that can energize electrode 42.

Introduction needle 32 includes a visible marker 50 that is a fixed distance 52 from the pointed tip 54 of introduction needle 32. Distance 52 is approximately the same as the length 56 of electrode 42. As described below, a surgeon desiring to embed electrode 42 in tissue can penetrate the tissue with introduction needle 32, thereby creating a tract in the tissue. The surgeon can drive needle 32 in the tissue up to marker 50, then perforate the tissue to cause the needle to emerge. The resulting tract is approximately the same length as electrode 42.

The surgeon can pull introduction needle 32 through the tract, thereby pulling leader 36 and pigtail 38 through the tract as well. As described below, pigtail 38 elongates when placed in tension, allowing pigtail 38 to pass through the tract. As the surgeon pulls leader 36 and pigtail 38 thought the tract, electrode 42 advances through the tract. Stopper 44, which is sized to be unable to pass through the tract, engages the tissue and stops the advancement of electrode 42. In this way, electrode 42 becomes embedded in the tissue, with substantially all of electrode 42 remaining in the tract.

Figure 3:
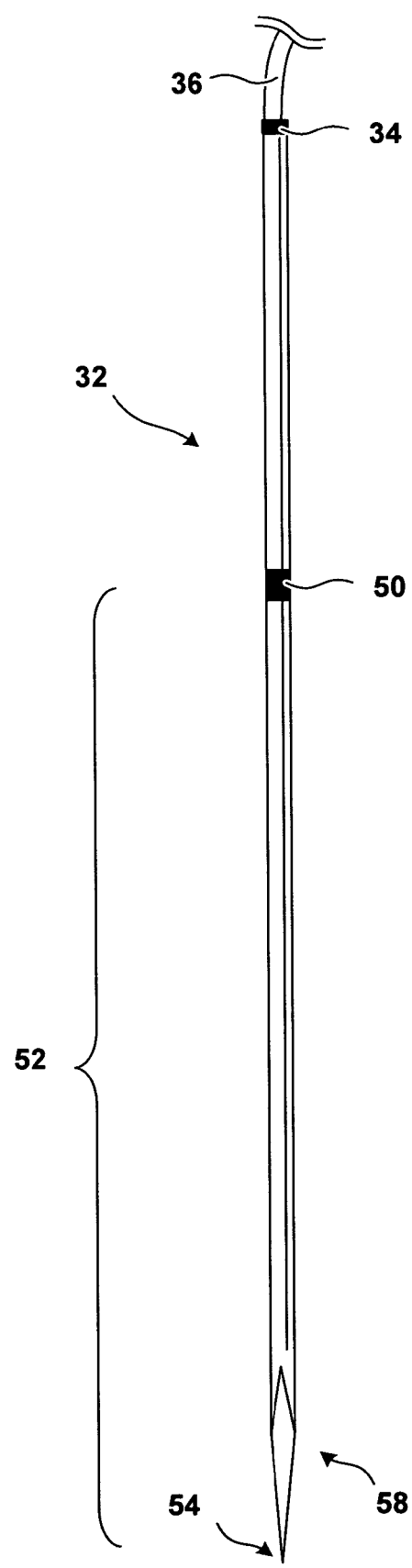
FIG. 3 is a schematic illustration of one embodiment of an introduction needle in the electrode assembly shown in FIG. 2.

FIG. 3 is a plan view of introduction needle 32 depicted in FIG. 2. Needle 32 is a straight surgical suture needle made of a durable material such as stainless steel. Needle 32 includes triangular point with a cutting edge 58, to facilitate penetration of tissue. The invention encompasses a variety of surgical needles, however, and is not limited to the device shown in FIG. 3.

Introduction needle 32 can be of any length and any grade. A typical introduction needle can be 0.8 millimeters in diameter and forty millimeters in length, but the invention is not limited to those dimensions. In some implementations, the characteristics of introduction needle 32 may depend upon the length 56 of electrode 42, the length of the desired tract, the resilience or firmness of the tissue to be penetrated, and the like. Introduction needle can be constructed from any of several standard materials, such as titanium, stainless steel and polycarbonate.

Marker 50 can be formed by any of several techniques. Marker 50 can be, for example, a colorant bonded to the metal of needle 32. Marker 50 can also be a groove etched onto needle 32. In some embodiments, a single needle 32 may include multiple markers, making needle 32 suitable for embedding electrodes of various lengths in tissue. Needle 32 can be treated with a chemical agent, such as an anti-inflammatory agent or an anti-coagulant, which elutes from needle 32 when needle 32 penetrates tissue.

Leader 36 is coupled to needle 32 via connecting element 34, which may be any element that affixes leader 36 to needle 32. Connecting element 34 may be a component of needle 32, such as an eye or a drilled hollow end, or may be a component of leader 36, or may be separate element that attaches needle 32 to leader 36. In the example shown in FIG. 3, needle 32 is an atraumatic surgical needle, with leader 36 being attached to needle 32 via a known technique such as crimping. The invention is not limited to any particular apparatus or technique for coupling leader 36 to needle 32.

Figure 4:
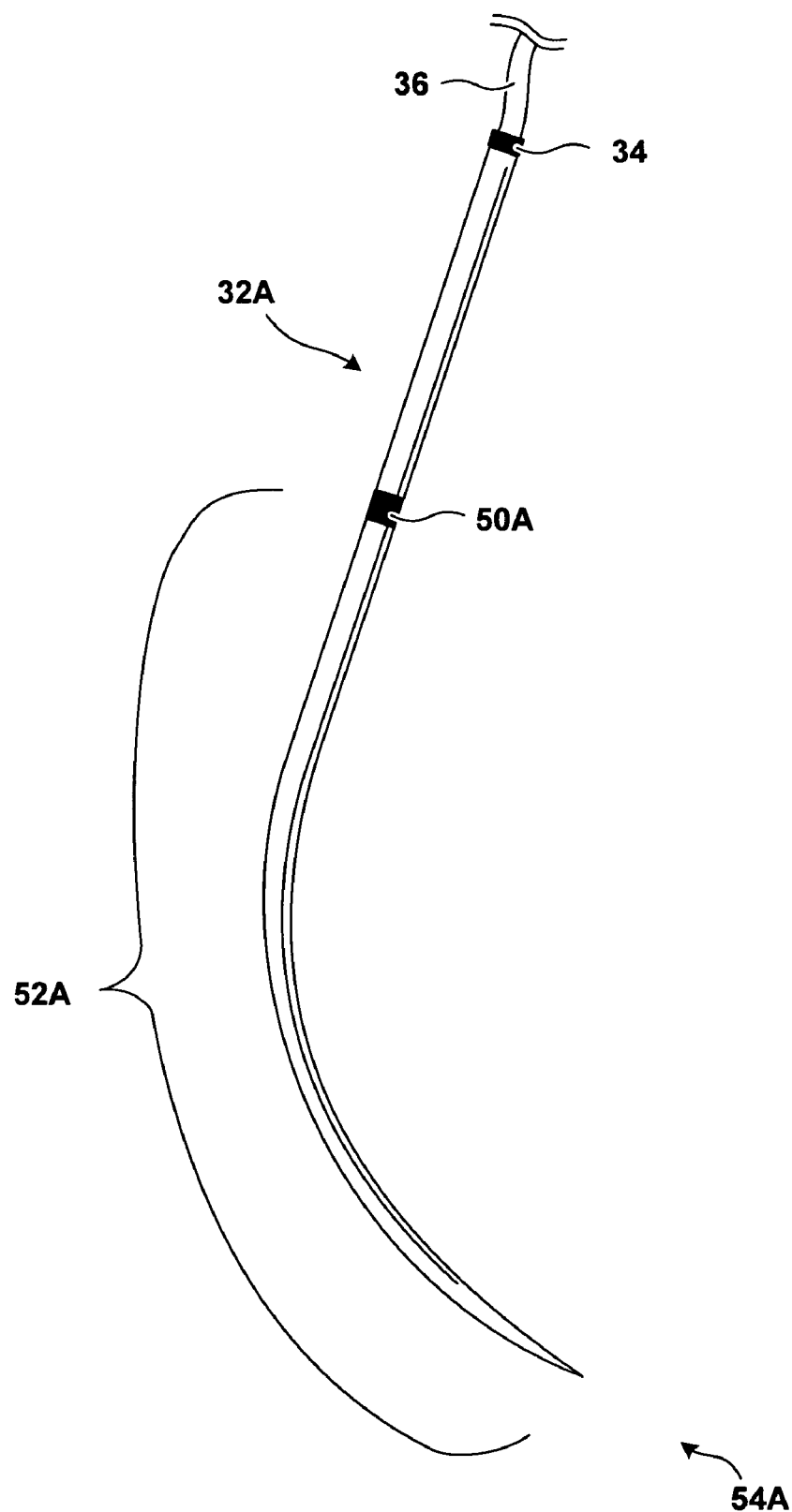
FIG. 4 is a schematic illustration of another embodiment of an introduction needle in an electrode assembly.

FIG. 4 is an alternate embodiment of an introduction needle 32A, in particular, a curved surgical needle. There are many types of curved surgical needles, and needle 32 is a half curved surgical needle. Curved needle 32A can be useful when the surgeon desires to create a curved tract in the tissue, or when the surgeon desires additional leverage to cause needle 32A to perforate the tissue. As with straight introduction needle 32, curved needle 32A includes a marker 50A that is a fixed distance 52A from tip 54A. Distance 52A is approximately the same as the length 56 of electrode 42, which will be embedded in the tissue.

Although the invention is not limited to any particular shape of introduction needle, straight needle 32 and half curved needle 32A may offer an advantage of working easily with a multiple needle driver, which will be described below.

Figure 5:
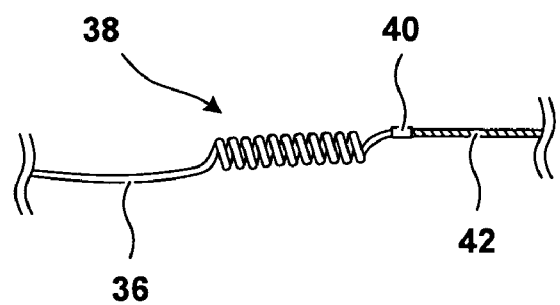
FIG. 5 is a schematic illustration of one embodiment of a fixation mechanism comprising a set of helical coils.
Figure 6:
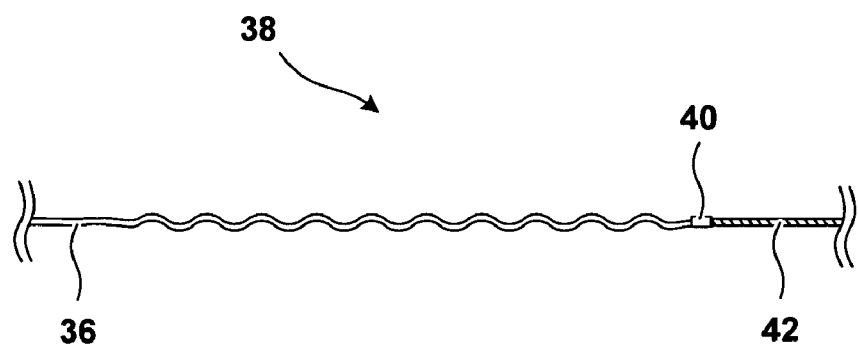
FIG. 6 is a schematic illustration of the embodiment of the fixation mechanism shown in FIG. 5, with the fixation mechanism under tension.
Figure 7:
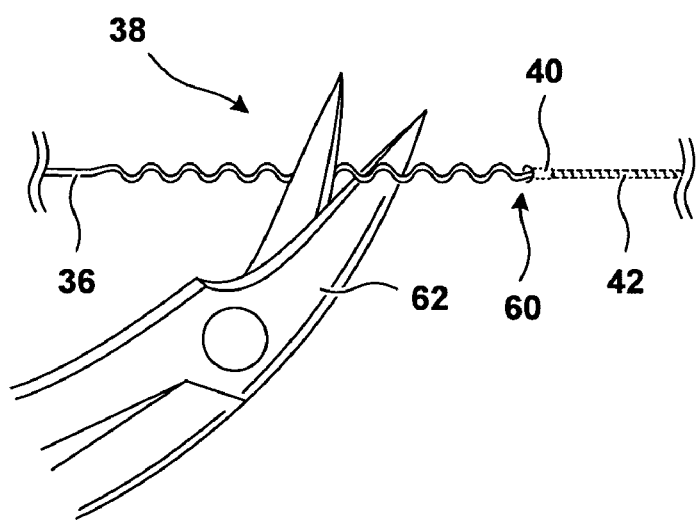
FIG. 7 is a schematic illustration of the embodiment of the fixation mechanism shown in FIG. 5 after the fixation mechanism has been pulled through tissue.

FIGS. 5-7 show leader 36 and pigtail 38 in more detail. In the embodiment depicted in FIGS. 5-7, pigtail 38 is a component structure of leader 36, sharing common materials. The invention also encompasses embodiments in which leader 36 and pigtail 38 are each formed from different materials. For example, leader 36 can be nylon surgical thread, and pigtail 38 can be formed from biocompatible polypropylene. In the discussion that follows, it will be assumed that leader 36 and pigtail 38 are formed from the same material.

In the embodiment shown in FIGS. 5-7, leader 36 and pigtail 38 are formed from a single length of biocompatible polypropylene, have a diameter of 0.4 millimeters and are able to withstand tension of about 8.9 N (2 lbs.). A typical length for leader 36 is 5 centimeters, but leader 36 may have any length.

In the embodiment shown in FIGS. 5-7, pigtail 38 can be formed by winding a portion of leader 36 around a core element, applying heat, and removing the core element. A typical pigtail 38 can include about a dozen turns, each turn having a diameter of about 1.3 millimeters when pigtail 38 is in its original configuration, as shown in FIG. 5. The invention is not limited to fixation mechanisms that have helical coils, but also includes fixation mechanisms that include waves, scrolls or any combination thereof.

Pigtail 38 can be formed from bioabsorbable or non-bioabsorbable material. It may be desirable, however, that pigtail 38 be made of a non-bioabsorbable material so that pigtail 38 can serve as a fixation mechanism for an extended period of time. Pigtail 38 can be treated with a chemical agent, such as an anti-inflammatory agent, a steroid or an antibiotic agent, that elutes from pigtail 38 to the nearby tissue. Such a drug can help reduce inflammation, irritation or risk of infection.

FIG. 6 shows what happens to pigtail 38 when leader 36 is placed in tension. As a surgeon pulls needle 32 through the tract in the tissue, leader 36 follows in the tract formed by needle 32. Pulling places leader 36 in tension. Pigtail 38 responds to tension by elongating and straightening. In this elongated configuration, pigtail 38 can be drawn through the tract without substantially enlarging or tearing the tract.

FIG. 7 shows pigtail 38 after pigtail 38 has been pulled through the tract in the tissue. In FIG. 7, electrode 42 is deployed beneath the surface of the tissue. Coupling element 40, which couples electrode 42 to pigtail 38, is deployed proximate to perforation 60 in the tissue. As a result, electrode 42 is buried inside the tissue but pigtail 38 is outside the tissue. When tension in pigtail 38 is relaxed, as depicted in FIG. 7, pigtail 38 returns to a more coiled configuration. In this coiled configuration, pigtail 38 resists re-entry into perforation 60. In this way, pigtail 38 serves as a distal fixation member that resists migration of electrode 42 in the proximal direction.

Once pigtail 38 is drawn through the tract and electrode 42 is deployed as shown in FIG. 7, the surgeon can cut pigtail 38 with a scissors 62, thereby disengaging needle 32 from electrode assembly 30. Some coils of pigtail 38 remain as a distal fixation member. The surgeon has discretion as to how many coils will remain attached to electrode 42, but typically three to five coils is sufficient to prevent migration.

Coupling element 40 couples leader 36 to electrode 42. Leader 36 and pigtail 38 are nonconductive. Coupling element 40 can be non-conductive or conductive. In one embodiment, coupling element is a made of a biocompatible metal, such as platinum, and is crimped to couple leader 36 to electrode 42. In this embodiment, coupling element 40 serves as an electrode tip deployed on the distal end of electrode 42.

Figure 8:
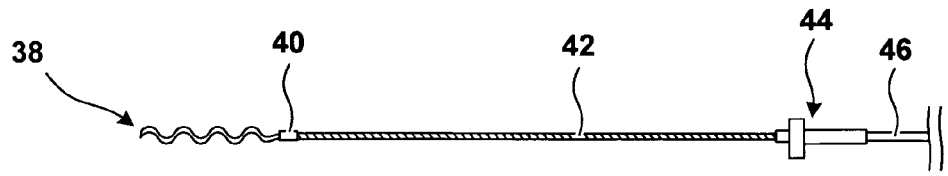
FIG. 8 is a schematic illustration of the embodiment of the stimulation electrode shown in FIG. 2.

FIG. 8 shows electrode 42 in more detail. Electrode 42 is made from a biocompatible metal appropriate for long-term implantation in a patient, such as platinum or a platinized (platinum-coated) metal. Electrode 42 can include any number of filaments, and can be coiled, twisted, braided or stranded for any desired degree of flexibility and strength. It is usually desirable for electrode 42 to be flexible, so as to follow the tract in the tissue and to accommodate motion of the tissue, such as contractive motion. Electrode 42 can be any length, but lengths generally would be between about ten and fifty millimeters, with a typical length being about thirty millimeters.

Electrode 42 may be provided with a chemical agent to promote one or more benefits to the patient. The agent may be provided by coating electrode 42 or by embedding the agent in electrode 42. After implantation of electrode 42, the chemical agent may elute from electrode 42 to the surrounding tissue. Examples of chemical agents include an anti-inflammatory agent, which can reduce inflammation associated with implantation of electrode 42 in the tissue. Examples of anti-inflammatory agents include Dexamethasone, Beclomethasone, Rapamycin, Ketorolac and Pentoxifylline. Various steroids can also reduce inflammation and can reduce fibrotic development that can accompany implantation of an electrode. An antithrombogenic or anticoagulant agent, such as heparin, coumadin, coumarin, protamine, and hirudin, can reduce risks associated with clotting. An antibiotic, antiseptic or anti-infection agent can reduce risks associated with infection. The above represent some agents that can be provided with electrode 42, but the invention is not limited to the agents herein described. In some embodiments of the invention, electrode 42 includes no chemical agent.

Figure 9:
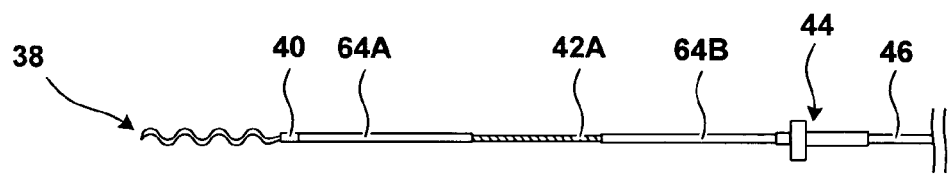
FIG. 9 is a schematic illustration of another embodiment of a stimulation electrode with at least one exposed portion and at least one insulated portion.
Figure 10:
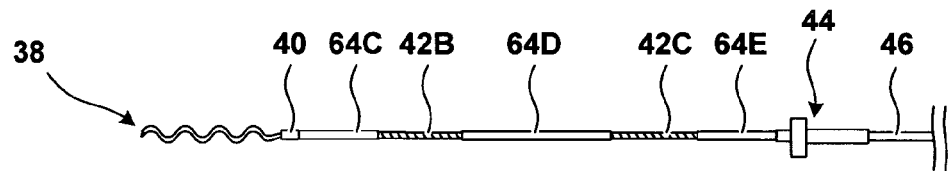
FIG. 10 is a schematic illustration of a further embodiment of a stimulation electrode with at least one exposed portion and at least one insulated portion.

In FIGS. 9 and 10 at least a portion of electrode 42 is covered by insulation. In FIG. 9, an exposed portion of electrode 42A is flanked by insulated portions 64A and 64B. When deployed, exposed portion 42A and insulated portions 64A and 64B would be deployed inside the tissue of the patient. Exposed portion 42A would be able to deliver electrical stimulation to the tissue, and insulated portions 64A and 64B would not be able to deliver electrical stimulation to the tissue. In FIG. 10, two exposed portions 42B and 42C would be embedded in the tissue, as would be three insulated portions 64C, 64D and 64E. Insulated portions 64A-64E can comprise any kind of biocompatible insulation, such as polyurethane, silicone, a polyurethane-silicone hybrid, or fluoropolymers such as Polytetrafluoroethylene (PTFE) or Ethylene/Tetrafluoroethylene Copolymer (ETFE).

A potential advantage of having electrode 42 partially insulated and partially exposed is that the region of stimulation can be regulated. In some patients, stimulation along the full length of electrode 42 may not be prudent, and it may be desirable to stimulate the tissue at targeted sites. In addition, multiple exposed portions of electrode 42 enable stimulation at multiple targeted sites, which may be advantageous in neurostimulation or other applications. Further, control of the degree of exposure of electrode 42 enables control of the shape of the electric field attendant to stimulation, as described in more detail below, reducing the risk of stimulation of tissues not targeted for stimulation. The invention is not limited to any particular number of exposed portions of electrode 42, or to any length or position thereof. The length and position of an exposed portion of electrode 42 can be determined by a physician for the patient.

Figure 11:
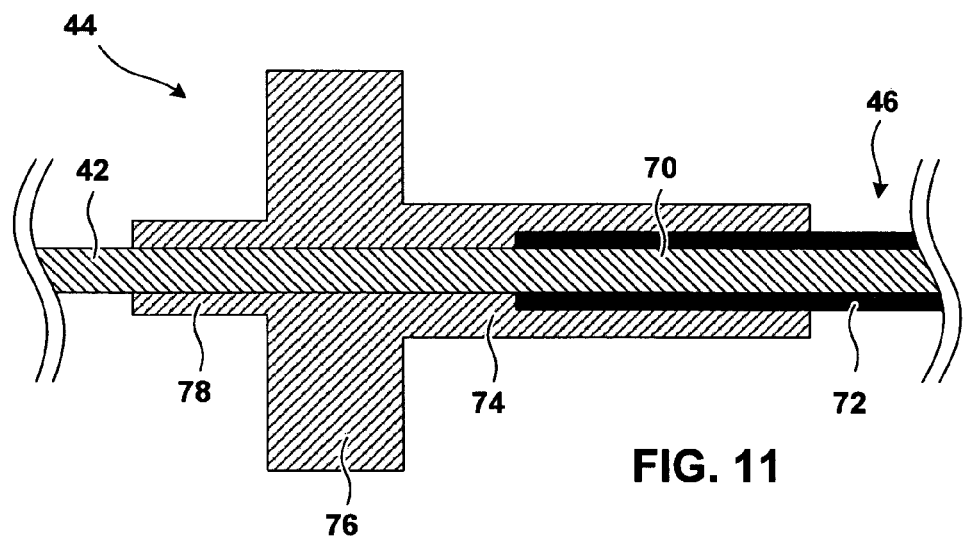
FIG. 11 is a cross-sectional view of the embodiment of the stopper in the electrode assembly shown in FIG. 2.

FIG. 11 shows a cross-section of a typical stopper 44. Stopper 44 can be constructed from any of several biocompatible materials and can be formed by any technique. For example, stopper 44 can be constructed of molded silicone rubber. In the embodiment shown in FIG. 11, stopper 44 is the interface between electrode 42 and insulated lead body 46. In particular, insulated lead body 46 comprises a conductor 70 that is electrically contiguous with electrode 42, surrounded by insulation 72. Insulation 72 can be any biocompatible insulation, such as those mentioned previously.

In the embodiment shown in FIG. 11, stopper 44 includes a substantially cylindrical main body 74, with a disk-shaped member 76. A typical length for main body 74 is about eight to ten millimeters. Disk-shaped member 76 may be about two millimeters thick and about three to six millimeters in diameter. In general, disk-shaped member 76 is sized to be too large to enter the tract created by needle 32. A disk-shaped member may have a diameter of three or more times that of the diameter of the introduction needle.

As electrode 42 is drawn through the tract in the tissue, disk-shaped member 76 of stopper 44 engages with the tissue and does not enter the tract, thereby resisting further advancement of electrode 42 through the tract. As shown in FIG. 11, stopper 44 can also include an interface member 78 that secures the interface between electrode 42 and stopper 44, and that helps keep disk-shaped member 76 properly oriented with respect to electrode 42.

Figure 12:
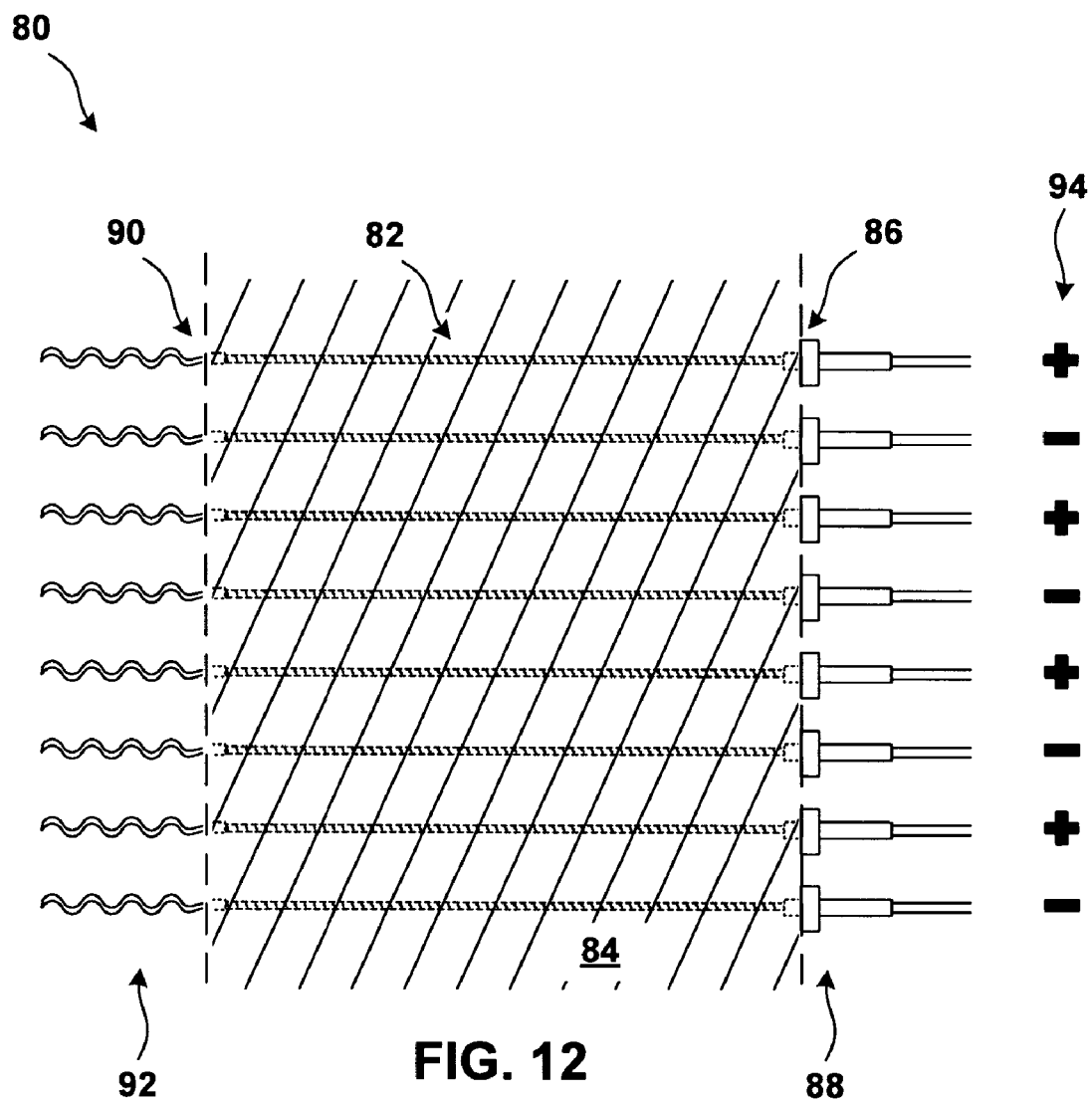
FIG. 12 is a schematic diagram illustrating cooperation of a set of electrode assemblies.

FIG. 12 is a schematic diagram illustrating cooperation of a set of electrode assemblies 80. Electrodes 82 of electrode assemblies 80 are substantially embedded in tissue 84. Along a perforation entry line 86, stoppers 88 act as proximal fixation mechanisms to prevent electrodes 82 from advancing distally. Along a perforation exit line 90, pigtails 92 act as distal fixation mechanisms to prevent electrodes 82 from advancing proximally.

Electrodes 82 are deployed substantially parallel to one another. Further, as shown by polarity indicators 94, electrodes 82 alternate in polarity, with alternating electrodes 94 having high and low potential during delivery of a stimulation to tissue 84. In this deployment, the electrical field created by electrodes 82 is substantially perpendicular to the orientation of electrodes 82, with reduced fringing fields. In other words, the electrical field is more localized, and the electrical field can be directed to stimulate target tissue, with less risk of stimulating tissues that are not targeted for stimulation.

Furthermore, electrodes 82 deployed as shown in FIG. 12 can stimulate tissue 84 by applying lower voltages. If, for example, an electrical field strength of one volt per millimeter of tissue is to be achieved using a conventional electrode deployment, in which a current path is provided between only two electrodes, an IPG generates a stimulation having a relatively high voltage difference between the electrodes. A region of target tissue can be several millimeters across, and the stimulation voltage from a conventional electrode deployment would depend upon the size of the target tissue.

For purposes of illustration, tissue 84 shown in FIG. 12 can be thirty-five millimeters across, or more. Stimulating tissue in a target region with only two electrodes placed thirty-five millimeters apart would call for a thirty-five volt stimulation, i.e., one volt per millimeter of tissue. When multiple electrodes 82 are deployed throughout target region 84 as shown in FIG. 12, however, the distance between electrodes is reduced, and the voltage that will stimulate the tissue is also reduced. If, for example, electrodes 82 are deployed five millimeters from one another, the voltage potential between neighboring electrodes can be five volts.

When multiple electrodes 82 are deployed throughout target region 84, the lower stimulation voltage places less demand on the IPG. As a result, the IPG can usually generate the stimulations more quickly, with reduced drain on the power supply for the IPG.

A surgeon can implant electrodes 82 in tissue 84 one at a time, using electrode assemblies such as electrode assembly 30 shown in FIG. 2. In the interest of efficiency and promoting even spacing of electrodes, the surgeon may choose to introduce several electrode assemblies into the tissue as a group.

Figure 13:
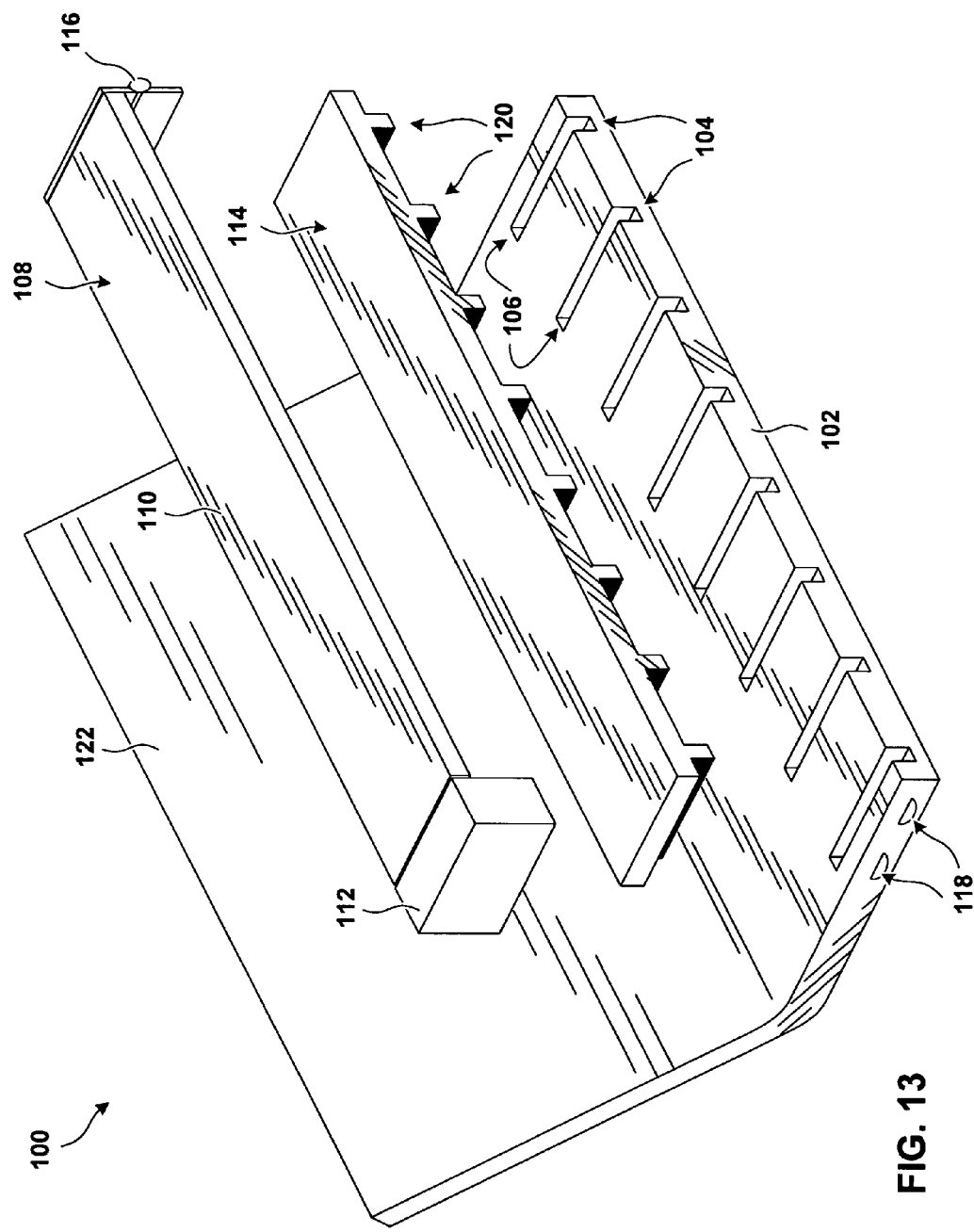
FIG. 13 is a perspective exploded diagram of an embodiment of a needle driver.

FIG. 13 depicts an apparatus 100 that can be used to introduce several electrode assemblies as a group. Apparatus 100 is a needle driver that is configured to receive needles from a plurality of electrode assemblies, and to introduce the needles into the tissue parallel to one another and consistently spaced. Needle driver 100 comprises a main body 102 having a plurality of trenches 104 configured to receive needles of one or more electrode assemblies. Main body 102 can be constructed of any durable material, including metals and polymers.

In FIG. 13, eight trenches are shown, but needle driver 100 may have any number of trenches. Trenches 104 are sized to receive the introduction needles. A typical trench 104 may be about 0.7 millimeters wide and about two millimeters deep. Trenches 104 may be separated laterally from one another by about five millimeters, such that needles placed in trenches 104 will be aimed in a direction parallel to one another and about five millimeters apart.

Each trench 104 may be about ten to fifteen millimeters long, but the invention encompasses other dimensions as well. The end 106 of trench 104 serves as a stop that bears against the needle and drives the needle through the tissue. Main body 102 is constructed of a material that will not yield, deform or otherwise fail when driving needles into tissue.

Figure 14:
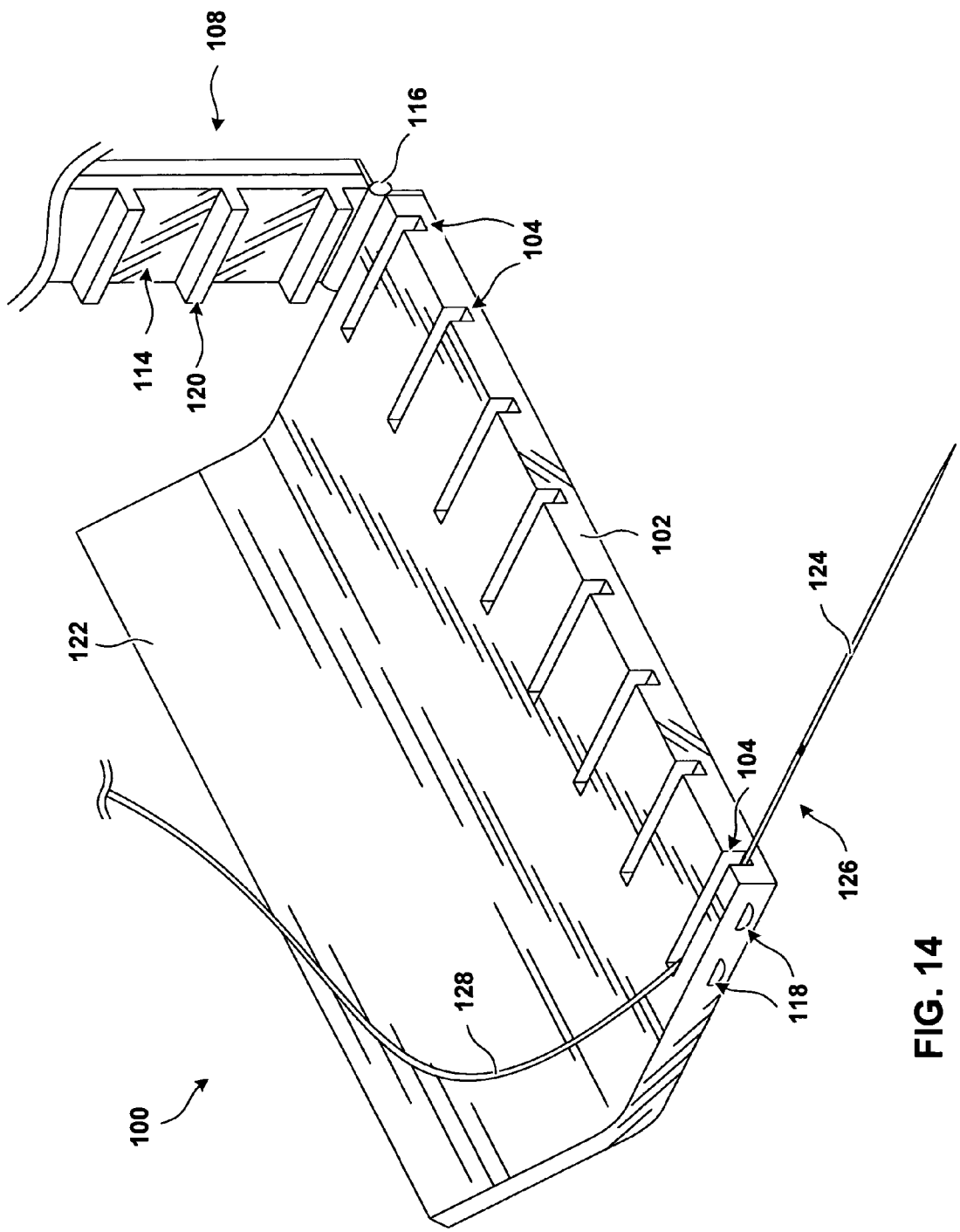
FIG. 14 is a perspective diagram of the needle driver shown in FIG. 13 with the cover open and an exemplary introduction needle in a trench of the needle driver.

A cover 108 comprising a lid 110, locking element 112 and fitting 114 is coupled to main body 102 by a hinge 116. The hinged coupling is shown in FIG. 14. Lid 110 may be constructed from any durable material, including metals, polymers and glass, and can be constructed from the same material as main body 102. Locking element 112 can be any kind of locking element, including but not limited to a hasp, a clamp, a bolt, a screw, or a latch. Locking element 112 is depicted as a spring-loaded mechanism that engages locking holes 118, but the invention is not limited to this particular embodiment.

Fitting 114 is typically fastened to the underside of lid 110. Fitting 114 is formed from a pliable material such as silicone rubber, and is configured to hold needles securely in trenches 104 with friction. Fitting 114 includes a plurality of projections 120 sized, shaped and spaced to fit in trenches 104. Projections 120 need not extend all the way back to stops 106, but may leave space for passage of a leader, as described below. When cover 108 is closed, fitting 114 bears against the needles in trenches 104 and holds the needles securely.

Needle driver 100 can further include a grippable structure 122. Grippable structure 122 enables the surgeon to take a secure hold of needle driver 100, maneuver needle driver 100, and apply force and leverage to needle driver 100. As depicted in FIG. 13, grippable structure 122 is integrally formed as a single piece with main body 102, and is oriented at approximately an angle of 135 degrees with respect to main body 102. The invention is not limited to the particular grippable structure 122 shown in FIG. 13, however. Grippable structure 122 can be any structure, including a handle, forceps, knob, grip, and the like. Grippable structure 122 can include structure to make grippable structure 122 more readily grippable, such as a textured or roughened surface or a non-slip coating.

FIG. 14 shows a needle 124 of an electrode assembly 126 being loaded into needle driver 100. Cover 108 is in an open position. Needle 124 is placed inside trench 104, with leader 128 extending out of trench 104. Any number of needles can be loaded in this fashion. Closing cover 108 and engaging locking element 112 secures needles 124 in needle driver 100. Needles need not be loaded one at a time. The invention supports, for example, the use of a loading apparatus that holds a desired number of needles and that enable several needles to be inserted into trenches simultaneously.

Figure 15:
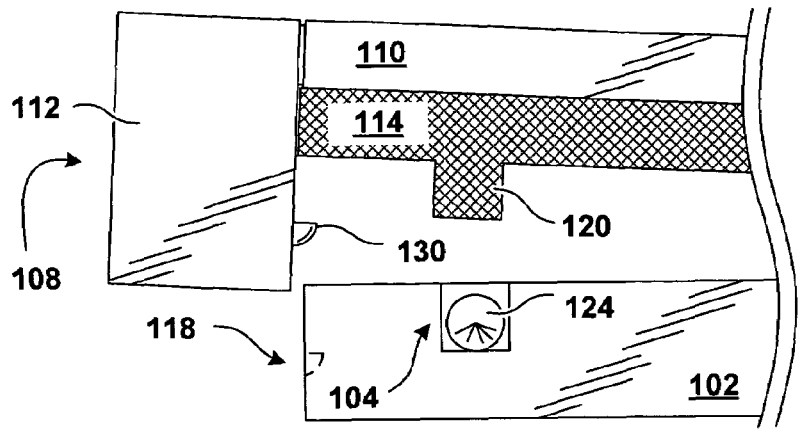
FIGS. 15-17 are plan views of the needle driver shown in FIG. 13, showing an introduction needle being secured in a trench.
Figure 16:
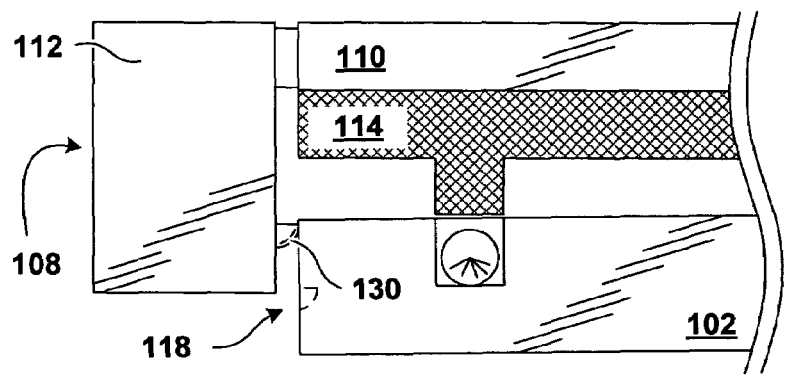
Figure 17:
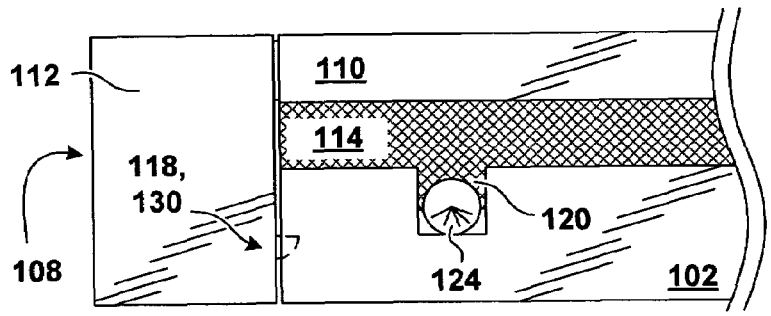

FIGS. 15-17 illustrate how closing cover 108 secures needles 124 in needle driver 100. Cover 108 hingedly swings from an open position toward a closed position, as shown in FIG. 15. Locking element 112 includes a catch 130. As catch 130 encounters main body 102 of needle driver 100, catch 130 pushes locking element 112, as shown in FIG. 16. Locking element 112 is spring connected to lid 110. As cover is further pressed to a closed position, protrusion 120 of fitting 114 deforms to seize needle 124 and hold needle 124 securely in trench 104. When catch 130 engages locking hole 118, locking element 112 springs back toward lid 110, seating catch 130 in locking hole 118, as shown in FIG. 17. In this way, cover 108 is held securely in a closed position, thereby securing needles 124 in trenches 104. The invention is not limited to the particular locations of hinge 116 and locking element 112 shown in the figures. For example, a mirror-image configuration of needle driver 100, with hinge 116 and locking element 112 on opposite sides, may be useful for left-handed personnel.

The invention supports embodiments in which a medical care providers load needles 124 of electrode assemblies into needle driver 100, according to the needs of the patient. The invention also supports embodiments in which needle driver 100 comes to the medical provider already loaded in a hermetically sealed package. The electrode assemblies and needle driver 100 can be pre-packaged and pre-sterilized, and the surgeon can select the package that is best suited to the patient's needs. The surgeon may select a package having a desired number of electrodes and needles, for example, or a package that includes electrodes of a desired length. During a surgical procedure, the package can be opened, a needle cap or caps that protect the tips of the needles can be removed, and the needle driver is ready for use. The package can be constructed from any number of materials, including plastic and metal foil.

During a surgical implantation procedure, a surgeon will use needle driver 100 to drive needles 124 through tissue to create tracts. Although the embodiments depicted in the figures show the creation of tracts by the application of force, the invention supports embodiments in which mechanical advantage or other techniques help create tracts. For example, introduction needles may be rotated, pulsed with multiple impacts, or vibrated to help push the needles into the tissue. Once the tracts are made, the surgeon will not implant needle driver 100 in the patient. Accordingly, needle driver 100 is configured to secure needles 124 and to disengage from needles 124 as well.

Figure 18:
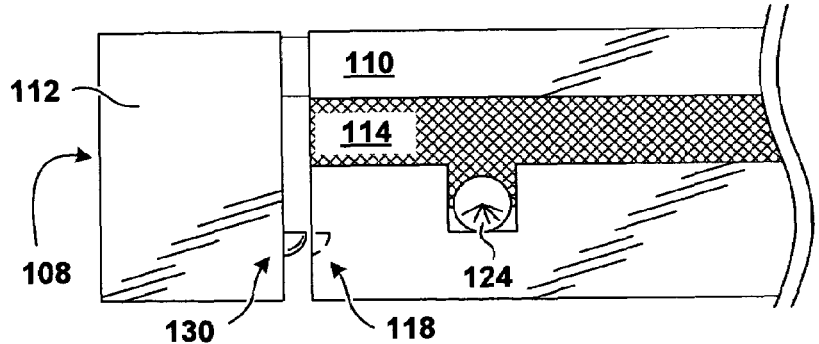
FIG. 18 is a plan view of the needle driver shown in FIG. 13, showing and exemplary locking mechanism.

FIG. 18 illustrates unlocking cover 108 so that needles 124 can be disengaged from needle driver 100. The surgeon pulls locking mechanism 112 away from lid 110, causing catch 130 to disengage from locking hole 118. The surgeon may swing open cover 108 and disengage needles 124 from needle driver 100.

Figure 19:
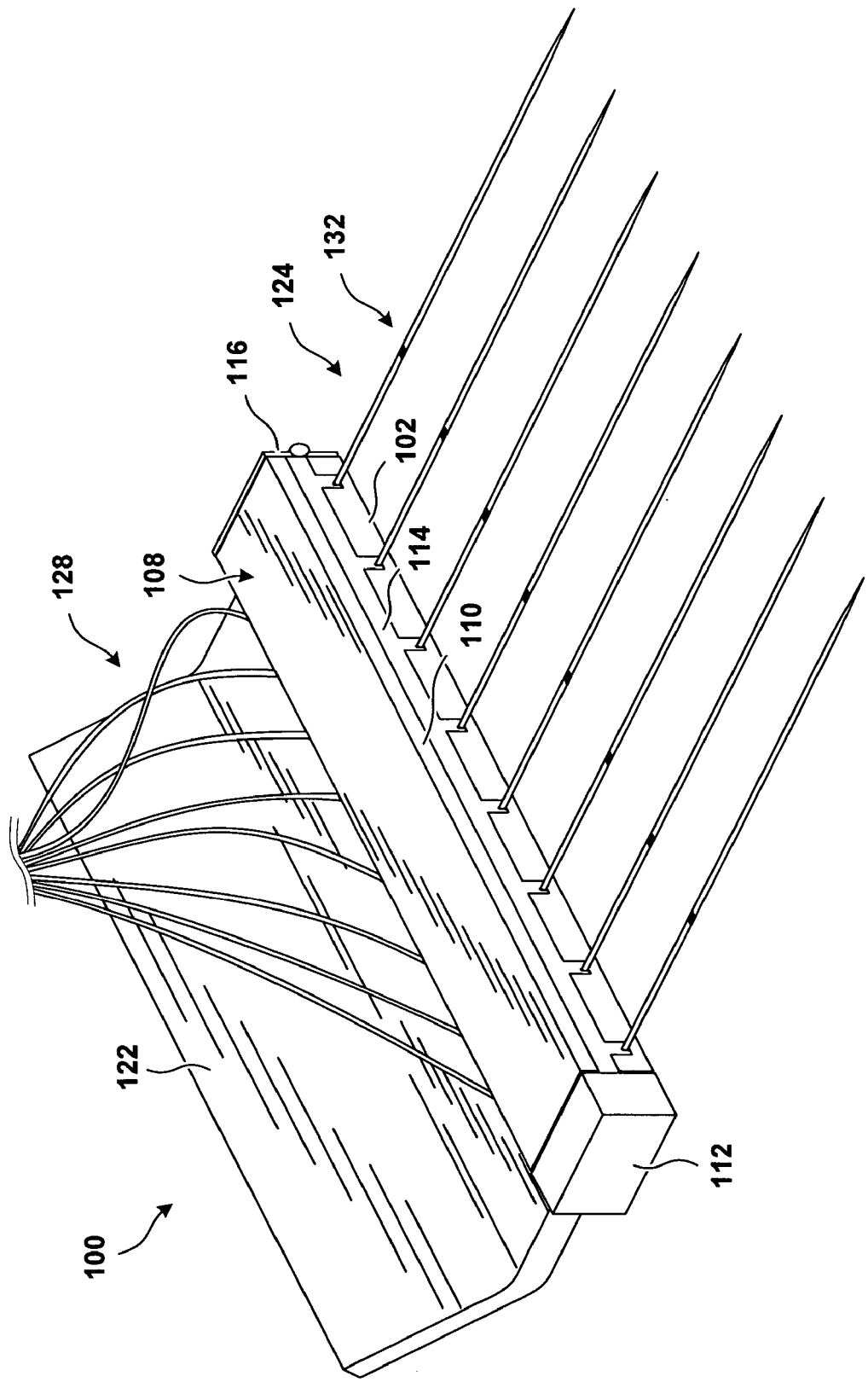
FIG. 19 is a perspective view of the needle driver shown in FIG. 13 loaded with introduction needles.

FIG. 19 shows a loaded needle driver 100, with needles 124 held securely. Markers 132 on needles 124 are visible, allowing the surgeon to regulate the length of the tract made by each needle 124. Leaders 128 are draped to one side.

Figure 20:
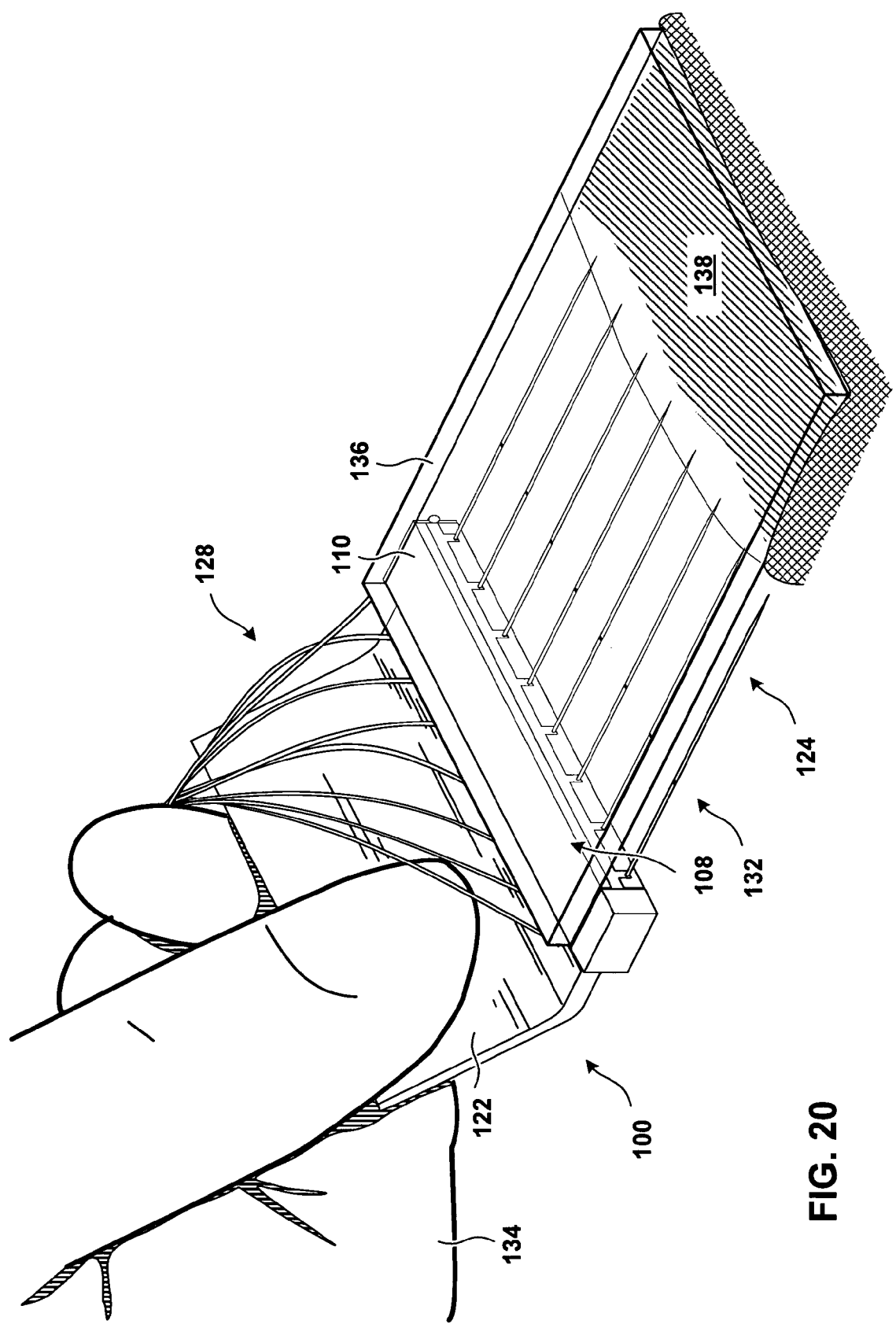
FIG. 20 is a perspective view of the needle driver with a stabilizer being used to introduce introduction needles into tissue.
Figure 21:
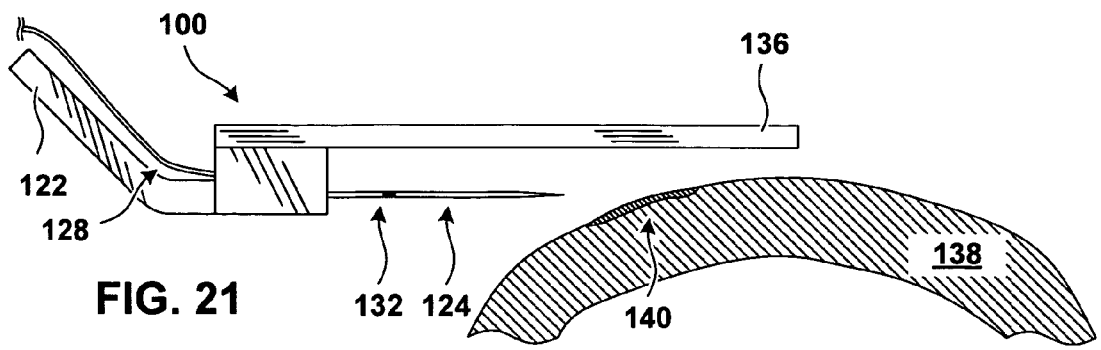
FIGS. 21-25 are conceptual diagrams illustrating creation of a tract in tissue with a needle driver such as that depicted in FIG. 20.

FIG. 20 shows a surgeon 134 holding loaded needle driver 100 by gripping grippable structure 122. Leaders 128 are draped to one side and are out of the way. In the embodiment of needle driver 100 shown in FIG. 20, needle driver includes a stabilizer 136. In the embodiment depicted in FIG. 20, stabilizer 136 is affixed to lid 110 of cover 108, but the invention also supports embodiments in which stabilizer 136 is affixed to other components of needle driver 100. Stabilizer 136 may be, but need not be, affixed in a permanent fashion. In some embodiments, stabilizer 136 can be adjusted or removed when, for example, stabilizer 136 takes too much room or otherwise interferes with the creation of tracts. Stabilizer 136 is transparent, allowing surgeon 134 to see needles 124, markers 132, and target tissue 138. Stabilizer 136 can be constructed of any solid transparent material, such as glass, acrylic or plastic, and preferably a material that is readily sterilized. Stabilizer 136 can be affixed to lid 110 in any manner, such as with adhesive, and can extend beyond the tips of needles 24 by a small distance, such as twenty millimeters.

Stabilizer 136 holds tissue 138 stable. Stabilizer 136 can further serve as a guide to determine tissue penetration depth. As surgeon 134 moves needles 124 proximate to tissue 138, tissue 138 may move or slide. In the case of an organ such as a beating heart, the organ can be in continuing motion. Stabilizer 136 helps hold a region of tissue 138 relatively still so that surgeon 134 can perforate tissue 138 in a more controlled fashion.

FIGS. 21-25 illustrate use of loaded needle driver 100 with stabilizer 138. A single needle 124 is shown for clarity. The surgeon (not shown) desires to implant a plurality of electrodes in target tissue 138, preferably beneath a desired stimulation region 140. As the surgeon brings needle driver 100 proximate to tissue 138, stabilizer 136 comes in contact with tissue 138 and holds tissue relatively still so that the surgeon can perforate tissue 138 in a desirable area. The surgeon can see tissue 138 and needles 124 through stabilizer 136.

Figure 22:
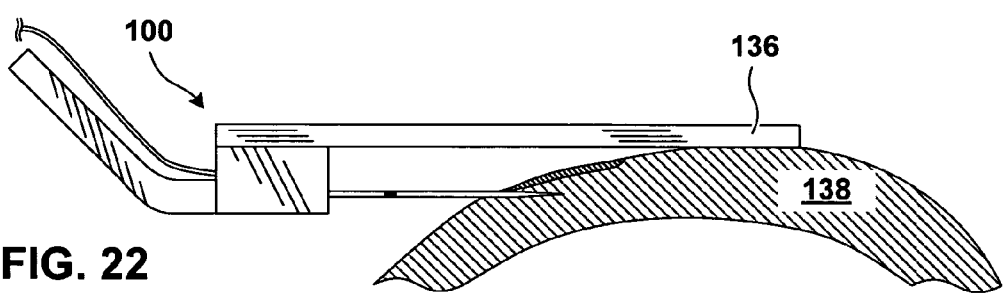
Figure 23:
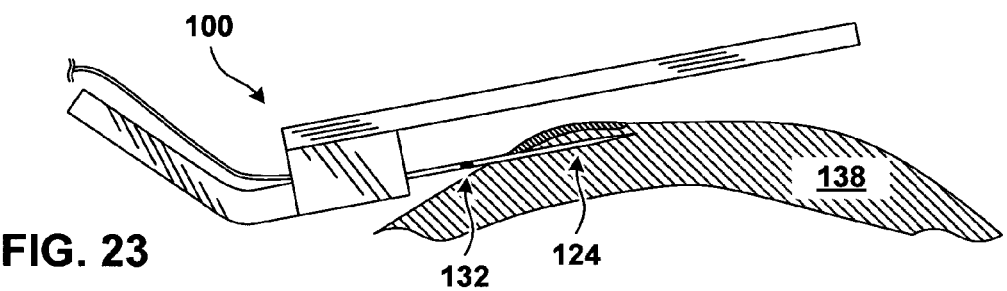
Figure 24:
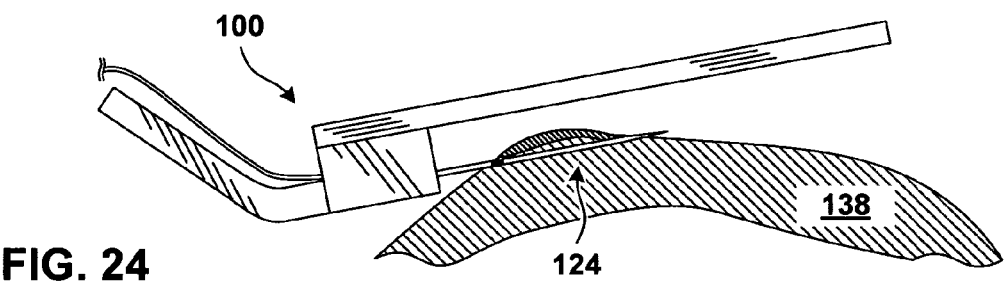

The surgeon can perforate the tissue with all needles 124 simultaneously, as shown in FIG. 22. FIG. 22 also illustrates how stabilizer 136 can serve as a tissue depth guide. The distance between needles 124 and stabilizer 136 is fixed, so stabilizer 136 prevents needles 124 from penetrating tissue 138 too deeply. When target tissue 138 is cardiac tissue, for example, stabilizer 138 helps prevent penetrating through the endocardium. As the surgeon drives needles 124 into tissue 138, the surgeon monitors progress by observing markers 132. As shown in FIG. 23, the surgeon may cause needles 124 to begin emerging from tissue 138 when markers 132 come close to entering tissue 138. Using markers 132 as guides, the surgeon can perforate tissue 138 and cause needles 124 to emerge, as shown in FIG. 24, thereby creating a plurality of parallel, regularly spaced tracts that are sized to receive the stimulation electrodes.

Figure 25:
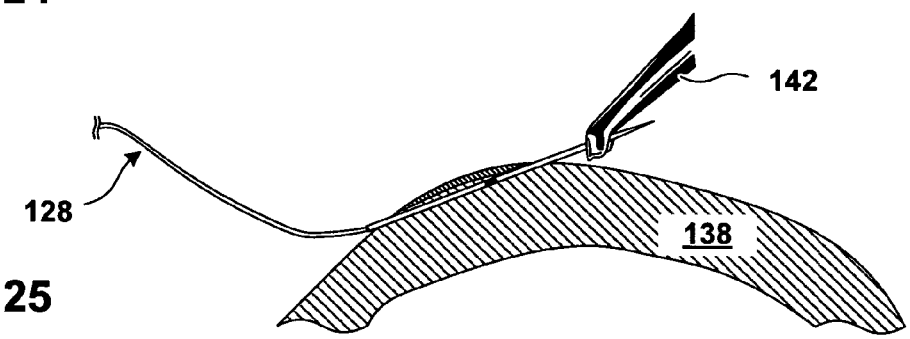

After the tracts are created, the surgeon disengages needle driver 100 from needles 124. The surgeon can unlock cover 108, allowing needles 124 to be disengaged from needle driver 100. Needle driver 100 is removed from the surgical field. Tissue 138 holds a plurality of needles 124. With an instrument such as a forceps 142, the surgeon pulls each needle 124 from tissue 138, as shown in FIG. 25. The surgeon draws leader 128 through the tract, followed by the stimulation electrode. A stopper on the proximal end of the stimulation electrode impedes further advancement of the electrode, and the electrode is substantially completely embedded in the tract. The surgeon then cuts the pigtail, as shown in FIG. 7, and discards the needle and leader. The surgeon repeats this process for the other needles in tissue 138.

Figure 26:
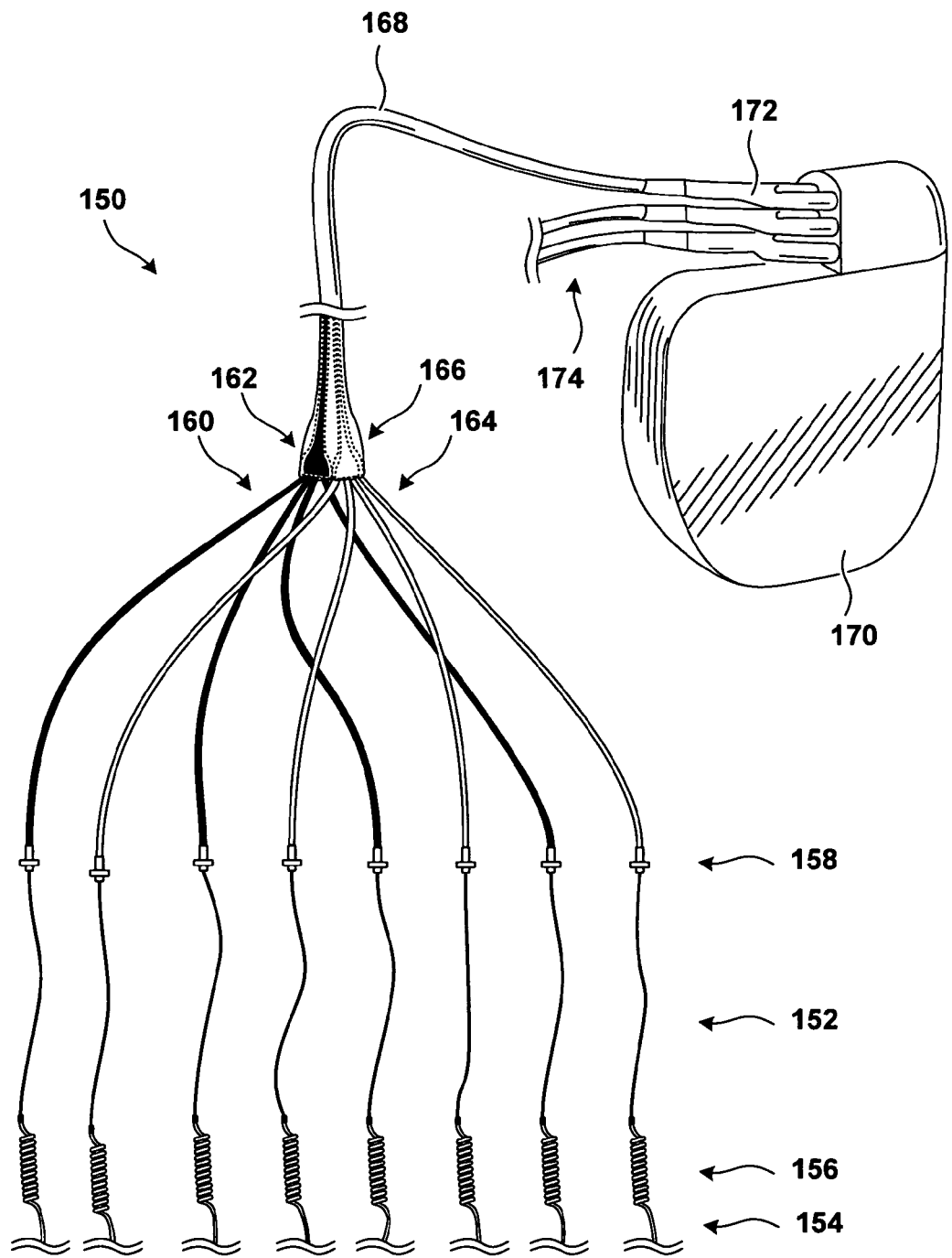
FIG. 26 is a system comprising a plurality of electrode assemblies in an array.

FIG. 26 illustrates an electrode array 150 that can be used with needle driver 100. Electrode array 150 is similar to a group of individual electrode assemblies 30 shown in FIG. 2, in that each electrode 152 is associated with an introduction needle (not shown in FIG. 26), a leader 154, a pigtail 156 and a stopper 158. Electrodes of like polarity, however, share lead wire. Electrodes having one polarity, denoted by black wires 160, are electrically coupled to one another at a node 162. Similarly, electrodes having the opposite polarity, denoted by white wires 164, are electrically coupled to on another at another node 166. Conductors for each polarity are combined into a single lead 168, which is electrically coupled to an IPG device 170 with a single IPG connector 172.

In the configuration shown in FIG. 26, electrodes 152 are not controlled independently. Instead, IPG device 170 delivers a single stimulation that drives one set of electrodes to a high electrical potential and drives the other set to a low electrical potential. In this way, electrode array 150, when implanted, operates as a stimulating unit. Although FIG. 26 depicts sets of electrodes that can be driven to two different voltage potentials, the invention also supports embodiments in which IPG device 170 generates more than two different voltage levels.

IPG device 170 can be any device configured to generate electrical stimuli. IPG device 170 can be a pulse generator that is dedicated to providing stimulation to electrodes 152. IPG device 170 can also be configured to perform other functions as well. In FIG. 26, IPG device is coupled to additional leads 174 that can be deployed elsewhere in the body of the patient. IPG device 170 can be, for example, a pacemaker, cardioverter-defibrillator, or neurostimulator.

Figure 27:
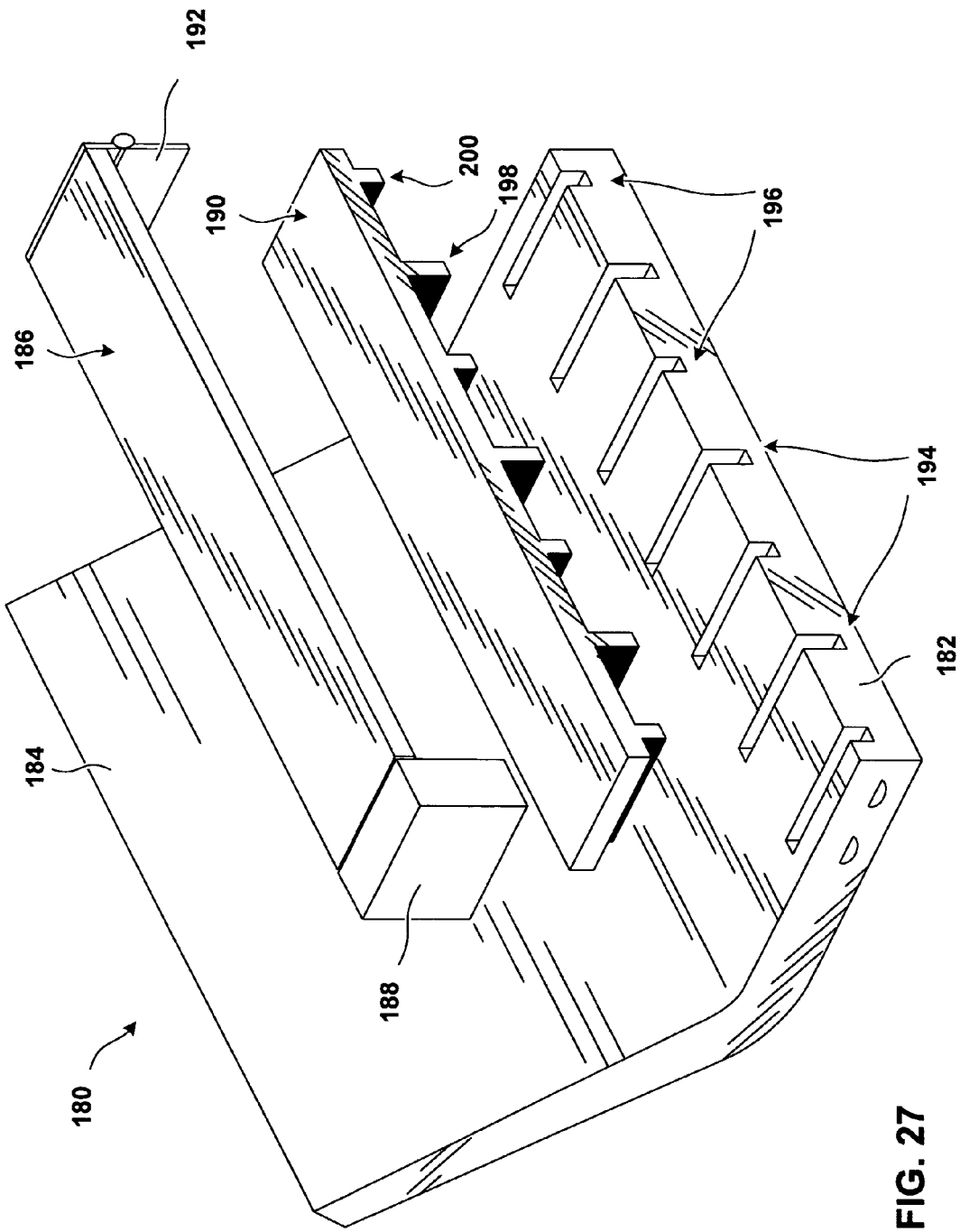
FIG. 27 is a perspective exploded diagram of another embodiment of a needle driver.

FIG. 27 shows another embodiment of a needle driver 180 that illustrates some of the variations. Needle driver 180 is similar in some respects to needle driver 100 shown in FIG. 8. Like needle driver 100, needle driver 180 is configured to receive needles from a plurality of electrode assemblies, and to introduce the needles into tissue parallel to one another and consistently spaced. Needle driver 180 comprises a main body 182, a grippable structure 184, a lid 186, a locking element 188, and a fitting 190. Lid 186 and fitting 190 can be coupled to main body 182 by a hinge 192.

Like needle driver 100, needle driver 180 includes trenches. Unlike needle driver 100, the trenches in needle driver 180 comprise deep trenches 194 and shallow trenches 196. The dimensions of shallow trenches 196 may be comparable to those of trenches 104 of needle driver 100. Deep trenches 194 are deeper than shallow trenches, such as by two to five millimeters deeper. Fitting 190 includes deep projections 120 sized, shaped and spaced to fit in deep trenches 194, and shallow projections 200 sized, shaped and spaced to fit in shallow trenches 196.

Needle drivers 100 and 180 can be loaded and used in a similar fashion. When a surgeon uses needle driver 180, however, the needles are non-planar. In particular, the needles in deep trenches 194 become more deeply embedded in the tissue than the needles in shallow trenches 196. As a result, the surgeon can create tracts, and implant stimulating electrodes, at different depths in the tissue. One possible application of such a non-planar arrangement may be to apply stimulation to a thick region of target tissue.

An additional distinction between needle driver 100 and needle driver 180 is that needle driver 180 is configured to receive up to seven needles, while needle driver 100 can receive up to eight needles. The invention can include trenches to accommodate any number of needles, and the number need not be an even number. A surgeon using needle driver 180 may choose, for example, to implant four high-voltage potential electrodes in the tissue, and three low-voltage potential electrodes interspersed between—but deeper in the tissue than—the high-voltage potential electrodes. To achieve this result, needles coupled by leaders to high-voltage potential electrodes could be loaded into shallow trenches 196, and needles coupled by leaders to low-voltage potential electrodes could be loaded into deep trenches 194.

EXAMPLE 1

The following example, which demonstrates some of the aspects of the invention, is for illustrative purposes. The subject of the test was an ex vivo porcine heart. Two electrode assemblies, like electrode assembly 30 shown in FIG. 2 but without stoppers, were introduced into the left ventricular wall of the heart. Each straight introduction needle was individually introduced into the myocardium and perforated out of the myocardium, creating a tract. The needle was then pulled out of the distal perforation in the myocardium, thereby pulling the leader into the tract.

Each leader included a pigtail. Pulling the leader caused the pigtail to elongate and straighten, as depicted in FIG. 6. Each pigtail was drawn through the respective tract without substantially enlarging or tearing the tract.

As each pigtail was drawn through the tract, a flexible electrode coupled to the pigtail became embedded in the tract. Each electrode was embedded about three millimeters deep in the tissue, at the deepest point, and could be seen through the slightly translucent myocardium. Each pigtail resisted re-entry into the tract, thereby serving as a distal fixation member that resisted migration of the electrode in the proximal direction and that did not harm the myocardium.

EXAMPLE 2

In another test, an ex vivo canine heart was used. Two electrode assemblies, like electrode assembly 30 shown in FIG. 2, including stoppers, were introduced into the left ventricular wall of the heart. Each straight introduction needle was individually introduced into the myocardium and perforated out of the myocardium, creating a tract. The length of the tract was targeted to be approximately thirty millimeters, which was the length of the electrode included in the assembly.

The needle was then pulled out of the distal perforation in the tissue, thereby pulling the leader into the tract. Pulling the leader caused the pigtail to elongate and straighten, and the pigtail was readily pulled through the tract, thereby pulling the flexible electrodes into the tract. As each pigtail emerged from the tract, stoppers on the proximal ends of the electrodes impeded further advancement of the electrodes in the tract.

When the stoppers came in contact with the myocardium, substantially all of the flexible electrodes were embedded in the tissue. It is estimated that the electrodes were five to ten millimeters deep at their deepest point, and that the myocardium itself was about twenty millimeters thick at this point. The introduction needles did not penetrate through the myocardium into the left ventricular chamber, and therefore the tract did not create any site for clotting inside the left ventricle.

Each pigtail served as a distal fixation member that resisted migration of the electrode in the proximal direction, and each stopper served as a proximal fixation member that resisted migration of the electrode in the distal direction.

EXAMPLE 3

In further tests, a needle driver similar to that depicted in FIG. 13, but configured to hold ten needles, was used to create ten tracts simultaneously in a canine heart. In an ex vivo test, ten tracts, each five millimeters apart and equidistantly spaced, were created in the myocardium. The needle driver could readily be used to drive ten needles at once. Further, it was demonstrated that the needle driver could control the depth of the tracts as well as the length of the tracts.

The needles were components of electrode assemblies similar to electrode assembly 30 shown in FIG. 2. It was demonstrated that the needle driver could be disengaged from the needles, and the needles could be pulled out of the myocardium to implant ten equidistantly spaced electrodes in the tissue.

In numerous ex vivo tests, a needle driver similar to that depicted in FIG. 13, with a stabilizer similar to that depicted in FIG. 20, was used to create six to eight tracts simultaneously in a beating canine heart. The needle driver could readily drive six to eight needles while controlling the depth and the length of the tracts. It was further demonstrated that the needle driver could be disengaged from the needles in a surgical setting. The electrodes of multiple electrode assemblies, each electrode assembly similar to electrode assembly 30 shown in FIG. 2, were implanted in an equidistant fashion in the myocardium.

The preceding examples are illustrative of an application of the invention, in connection with implantation of one or more electrodes. The invention is not limited to the particular test protocols described above. In particular, the invention is not limited to use with a heart, or with any particular needle driver or any particular number of electrode assemblies. Furthermore, the invention contemplates single electrode assemblies as well as electrode assemblies in an array.

The invention is not limited to any particular surgical procedure. The invention supports electrode implantations in addition to those specifically described herein. For example, the invention supports implantations in which the target tissue receives one set of electrodes at one depth and oriented in one direction, and another set at a different depth and oriented in a different direction. Nor is the invention limited to any particular scheme for stimulation of the target tissue. Different biological material may respond differently to electrical stimulation. Accordingly, an IMD may be programmed to apply a stimulation scheme that works best for the patient. In addition, the invention does not exclude other stimulation therapies. These and other embodiments are within the scope of the following claims.

The invention claimed is:

1. A device comprising:
   a loaded needle driver, the loaded needle driver comprising:
   a plurality of surgical needles, each of the needles comprising a proximal end and a distal tip,
   a main body having a plurality of trenches, each of the trenches configured to receive a respective one of the surgical needles, wherein the proximal ends of the surgical needles are secured in the respective trenches,
   a cover configured to assume an open position and a closed position, wherein the cover in the open position is configured to permit insertion of the surgical needles in the trenches and removal of the surgical needles from the trenches, wherein the cover in the closed position is configured to secure the surgical needles in the trenches, and wherein the cover comprises a fitting affixed to a lid, the fitting comprising a plurality of projections sized, shaped and spaced to fit into the trenches to secure the needles when the cover is in the closed position; and
   a package that contains the loaded needle driver.

2. The device of claim 1, further comprising a locking mechanism configured to assume a locked position and an unlocked position,
   wherein the locking mechanism in the locked position secures the cover in the closed position.

3. The device of claim 1, wherein the lid is made of a non-pliable material.

4. The device of claim 1, wherein the fitting is made of a pliable material.

5. The device of claim 1, further comprising a grippable structure attached to the main body.

6. The device of claim 1, further comprising a hinge coupled to the cover and the main body, the hinge configured to allow the cover to swing from the open position to the closed position.

7. The device of claim 1, wherein the trenches are configured to aim the surgical needles in a direction, the device further comprising a transparent stabilizer attached to at least one of the main body or the cover and configured to extend in the direction beyond the tips of the surgical needles when the surgical needles are in the trenches.

8. The device of claim 7, wherein the stabilizer is constructed of one of glass, acrylic or plastic.

9. The device of claim 7, wherein the stabilizer is removable.

10. The device of claim 7, wherein the stabilizer is adjustable.

11. The device of claim 1, further comprising a plurality of needle caps configured to protect the tips of the surgical needles.

12. The device of claim 1, wherein the plurality of trenches comprise:
    a first trench having a first depth; and
    a second trench having a second depth deeper than the first depth.

13. The device of claim 1, wherein the package is constructed of plastic.

14. The device of claim 1, wherein the package is constructed of metal foil.

15. The device of claim 1, wherein the main body, the cover and the surgical needles are sterile.

16. The device of claim 1, wherein the package is hermetically sealed.

17. The device of claim 1, further comprising, for each of the surgical needles:
    a flexible leader having a proximal end and a distal end, the distal end of the leader being coupled to the proximal end of the surgical needle;
    a first fixation mechanism having a proximal end and a distal end, the distal end of the first fixation mechanism being coupled to the proximal end of the leader;

a length of electrode having a proximal end and a distal end, the distal end of the electrode being coupled to the proximal end of the first fixation mechanism;

a second fixation mechanism having a proximal end and a distal end, the distal end of the second fixation mechanism being coupled to the proximal end of the electrode; and a lead body having a proximal end and a distal end, the distal end of the lead body being coupled one of the proximal end of the second fixation mechanism and the proximal end of the electrode, the lead body further comprising a conductor that is electrically contiguous with the electrode.

18. The device of claim 17, wherein each of the surgical needles includes a visible marker at a distance from the tip, and wherein the distance from the tip to the marker is approximately equal to the length of the electrode coupled to that needle.

* * * * *

UNITED STATES PATENT AND TRADEMARK OFFICE
CERTIFICATE OF CORRECTION

| | |
|---|---|
| PATENT NO. | : 7,647,122 B2 |
| APPLICATION NO. | : 11/189490 |
| DATED | : January 12, 2010 |
| INVENTOR(S) | : Chan et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1204 days.

Signed and Sealed this

Sixteenth Day of November, 2010

David J. Kappos
*Director of the United States Patent and Trademark Office*